United States Patent [19]

Strober

[11] Patent Number: 5,985,656
[45] Date of Patent: Nov. 16, 1999

[54] SUPPRESSOR AND PROGENITOR CELLS

[75] Inventor: Samuel S. Strober, Portola Valley, Calif.

[73] Assignee: The Board of Trustees of the Leland Stanford Junior University, Stanford, Calif.

[21] Appl. No.: 07/971,723

[22] Filed: Nov. 4, 1992

Related U.S. Application Data

[63] Continuation-in-part of application No. 07/931,210, Aug. 17, 1992, abandoned, which is a continuation-in-part of application No. 07/789,169, Nov. 5, 1991, abandoned, which is a continuation-in-part of application No. 06/873,583, Jun. 12, 1986, abandoned.

[51] Int. Cl.$^6$ ........................................................ C12N 5/08
[52] U.S. Cl. ..................... 435/325; 424/93.1; 424/93.21; 424/93.7; 424/93.71
[58] Field of Search ............................ 435/240.1, 240.21, 435/325; 424/93 R, 93 P, 93 U, 93.1, 93.21, 93.7, 93.71

[56] References Cited

PUBLICATIONS

Strober, 1989, *J. Immunol. 143:*1118.
Strober, 1987, *Transplant. Proceeding XIX:*88.
Strober, 1987, *J. Immunol. 138:*699.
Van Vlasselaer, 1991, *Cell Immunol. 136:*1.
Palathumpat, 1992, *J. Immunol. 148:*373.
Schmidt, 1992, *Blood 80:*3242.
Schwardron, 1989, *Transplant. 48:*107.
Hertel–Wulff, 1987, *J. Exp. Med. 166:*1168.
Noga et al. J. Leukocyte Biology 43:279 1988.
Berveristz et al. J. Immunol. 144:411–19 1990.
Strober Ann. Rev. Immunol. 1984 2:219–37.
Schwadron et al. J. Exp. Med. 297–310 Jul. 1985.
Hortel–Wulff et al. J. Immunol. 133(5):2791–96 1984.
Oseroff et al. J. Immunol. 132(1): Jan. 1984.
Hertel–Wulff et al. Trans. Proceedings vol. XVII(1):1121–23 1985.
Tortora Microbiology and Introduction pp. 88–90 1989.
Martin et al. British Journal of Hematology 63:187–98 1986.

*Primary Examiner*—Anthony C. Caputa
*Assistant Examiner*—Nancy A. Johnson
*Attorney, Agent, or Firm*—Pennie & Edmonds LLP

[57] ABSTRACT

Natural suppressor (NS) cells secrete a soluble protein suppressor factor (SF) which suppresses the mixed lymphocyte response. NS cells as described herein are null, i.e., have the phenotype IL-2R$^+$, CD3$^-$, CD4$^-$, CD8$^-$, TCRαβ$^-$, Ig$^-$, MAC-1$^-$, or are double negative suppressors (DNS); i.e., have the phenotype IL-2R$^+$, CD3$^+$, CD4$^-$, CD8$^-$, TCRαβ$^+$. Both NS and SF are useful in vivo to confer immunotolerance with respect to allogeneic transplants, and to effect immunosuppression. They also enhance engraftment of transplanted cells. A population of cells can be provided using density gradient separation techniques which is enriched in progenitor cells as identified by the presence of CD34 surface markers.

12 Claims, 7 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 16 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Peptide
       (B) LOCATION: 1
       (D) OTHER INFORMATION: /label= Xaa
           /note= "Xaa = unknown"

(ix) FEATURE:
       (A) NAME/KEY: Protein
       (B) LOCATION: 11
       (D) OTHER INFORMATION: /label= Xaa
           /note= "Xaa = Ala or Phe"

(ix) FEATURE:
       (A) NAME/KEY: Peptide
       (B) LOCATION: 13
       (D) OTHER INFORMATION: /label= Xaa
           /note= "Xaa = Lys or Leu"

(xi) SEQUENCE DESCRIPTION: SEQ ID NO:1:

```
Xaa Glu Asn Val Gly Leu Asn Glu Val Val Xaa Leu Xaa Tyr Gln Val
1               5                   10                  15
```

(2) INFORMATION FOR SEQ ID NO:2:

(i) SEQUENCE CHARACTERISTICS:
       (A) LENGTH: 11 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Peptide
       (B) LOCATION: 8
       (D) OTHER INFORMATION: /label= Xaa
           /note= "X = Lys or Leu"

(xi) SEQUENCE DESCRIPTION: SEQ ID NO:2:

```
Leu Asn Glu Val Val Ala Leu Xaa Tyr Gln Val
1               5                   10
```

SUPPRESSOR AND PROGENITOR CELLS

CROSS-REFERENCE TO RELATED APPLICATIONS

This is a continuation-in-part of U.S. patent application Ser. No. 07/931,210, filed Aug. 17, 1992, now abandoned, which is a continuation-in-part of U.S. patent application Ser. No. 07/789,169, filed Nov. 5, 1991, now abandoned, which is a continuation-of-part of U.S. patent application Ser. No. 06/873,583, filed Jun. 12, 1986, now abandoned.

TECHNICAL FIELD

The invention relates to suppressing immune response. More specifically, the invention concerns both fresh and cloned natural suppressor cells that are capable of eliciting immunosuppression in a host, including suppression of graft versus host disease and enhancing engraftment of transplanted cells and tissues. The invention also concerns a soluble immunosuppressive factor capable of suppressing immune response in response to transplantation or allergens and in the management of autoimmune disease.

BACKGROUND ART

"Immunotolerance" and "immunosuppression" are general terms to describe the compatibility of materials which would be normally expected to result in an immune response. When tissues or cells are transplanted into an allogeneic host, absent these or immunosuppressive conditions, the host immune system will mount an immune response to the foreign antigens (host-versus-graft disease), and, more seriously, the immunocompetent cells in the transplant may respond to the antigens contained in the host (graft-versus-host disease). Other unwanted immune responses include allergic reactions and autoimmune diseases. Under all of the foregoing conditions, it is desirable that the immune response be suppressed.

It has been known for years that neonatal mammals are capable of acquiring persistent immunotolerance with respect to allogeneic immunocompetent cells or to other antigenic substances administered within a few days after birth. For example, mice injected with allogeneic substances bearing the histocompatibility antigens are able later to accept skin grafts from donors of the previously injected genotype. More recently, it has been shown that this immunosuppressive property of neonates is simulated by adults subjected to total lymphoid irradiation (TLI), i.e., high dosages of radiation sustainable when nonlymphoid tissues are protected. Such radiation has been used in the treatment, for example, of Hodgkin's disease. Adult subjects who have been subjected to TLI are also capable of acquiring persistent immunotolerance to antigens administered within a few days of the completion of TLI.

The detailed mechanism by which neonates and TLI-treated subjects are capable of acquiring an immunotolerance with respect to antigens and cells administered within these windows is not understood. Both clonal deletion and active suppression paradigms have been proposed. The picture is further complicated by the presence of at least two types of suppressor cells in neonatal spleens. One type is represented by macrophage precursors, which suppress in vitro the antibody response to sheep red-blood cells. This activity is inhibited by indomethacin, and the cells are thus presumed to be prostaglandin dependent. The other type is represented by lymphocytes which inhibit the mixed leukocyte response (MLR). These cells are apparently prostaglandin independent. One group of cells in this class, "null" cells, lack the surface markers characteristic of T cells, B cells, or macrophages, and have morphologies similar to natural killer cells in that they are large granular lymphocytes which lack antigen specificity and which carry out their effective function without antigenic stimulation. The surface phenotype of these cells is Ig$^-$, CD4$^-$, CD8$^{31}$, CD3$^-$, MAC-1–, TCR$\alpha\beta^-$. This population of null suppressor cells has been designated, for purposes of symmetry with natural killer (NK) cells, natural suppressor (NS) cells (Oseroff, A., et al., *J Immunol* (1984) 132:101).

In addition to the null phenotypes, natural suppressor cells that contain the surface phenotype Ig$^-$, CD4$^-$, CD8$^-$, CD3$^+$, MAC-1$^-$, TCR$\alpha\beta^+$ have been recovered from the spleens of adult mice subjected to TLI. These "double negative" suppressors (DNS) can be propagated in vitro under proper conditions indefinitely (Hertel-Wulff, B., et al., *J Immunol* (1984) 133:2791–2796, incorporated herein by reference). These "DNS" cells can also be cloned from cells obtained from neonatal spleen, normal adult spleen and bone marrow. (The null cells described above have also been cloned from adult TLI spleen and from normal thymus.)

It has now been found that cloned DNS or null cells are capable, when administered in vivo, of suppressing graft-versus-host disease initiated by simultaneously administered immunocompetent cells. In addition, the propagated DNS and null cells secrete into supernatant media a soluble factor which is capable of suppressing the immune response as shown by the ability to suppress alloreactivity in the commonly used in vitro test (the mixed leukocyte reaction (MLR) mentioned above) and in vivo in suppressing the acute immune response referred to as graft-versus-host disease as well as encouraging engraftment of transplanted tissue.

Additional publications of the applicants subsequent to the filing of the parent application herein further describe the cells and secreted factor. The status of the suppressor activity of the NS cells in general was reviewed by Strober, S., *Ann Rev Immunol* (1984) 2:219; a further description of the cloned suppressor cell lines is provided by Schwadron, R. B., et al., *J Exp Med* (1985) 162:297, and by Schwadron, R. B., et al., *Transplantation* (1989), p. 107. Hertel-Wulff, B., et al.,*J Exp Med* (1987) 16:1168, describe the rearrangement and expression of T-cell receptor genes in the cloned NS cell lines. The verification of the surface phenotype of the cloned DNS cell lines as IL-2R$^+$, CD3$^+$, CD4$^-$, CD8$^-$ and TCR$\alpha\beta^+$ was described by Strober, S., et al., *J Immunol* (1989) 143:1118. The DNS cells are thus distinguished from the null NS cells which expresses neither T nor B cell markers (CD3$^-$, TCR$\alpha\beta^-$, Ig$^-$). However, both types (null and DNS) express the surface receptor for IL-2 (IL-2R). The null cells are thus CD3$^-$, Ig$^-$, TCR$\alpha\beta^-$, MAC-1$^-$, and IL-2R$^+$. A further description of the soluble factor was provided by Hertel-Wulff, B., et al., *J Immunol* (1988) 140:2633. A more recent paper by Palathumpat, V. et al., *J Immunol* (1992) 148:373–380 further describes separations of the double negative suppressor cells from bone marrow of murine subjects.

The ability to suppress the capacity of immunocompetent donor cells to effect graft-versus-host disease is of particular significance in view of the growing technology permitting successful allografts and organ transplants. Transfers of healthy tissues into recipients in need of them seems at present limited in the main by lack of immunotolerance with respect to the recipient. Thus, if the problem of graft-versus-host disease could be solved, the dangers associated with bone marrow transplants would be considerably reduced. In the case of whole organ transplants, rejection of the organ would be reduced.

In addition, encouraging engraftment of transplanted cells is of importance. It is well known that administration of allogeneic tissue in the form of bone marrow to either neonates or adults subjected to TLI during the "window" period will convert the recipient to a chimera, which will recognize as "self" both its own antigens and those of the alloantigen administered at this time. The formation of a chimera shows that engraftment has occurred. The chimeric character of the host is also such that subsequently introduced immunocompetent cells will not attack host tissue. These chimeras are thus not only specifically receptive to the simultaneously administered donor bone marrow, but also to other donor tissue. The chimeric recipient, therefore, will in the future be able to tolerate transplanted tissue from the original donor.

In effecting engraftment, cells enriched in the cell surface marker CD34 are known to be helpful, since this marker appears to characterize "stem" or "progenitor" cells. These cells are progenitors of the multiplicity of differentiated cells that are found in the blood, including monocytes, macrophage, lymphocytes, red blood cells and so forth. Thus, the capacity of transplanted cells to engraft will be dependent on the enrichment of the transplanted cells in cells which bear the CD34 marker.

The recipient normal adult host must, of course, be prevented from succumbing to an acute immune response effected by the originally administered bone marrow cells. The DNS and null NS cells are capable of muting the immediate immune response and any other antidonor response sufficiently to permit the generation of characteristics of the chimera. Both fresh and cloned DNS and null cells are also capable of preventing the in vivo graft versus host immune response. The secreted factor is capable of inhibiting the immune response of donor against host, and host against donor cells in vitro, and in vivo.

Both null and DNS cells and the factors secreted by them are therefore useful in providing immediate blocking of either the graft immune response against mammalian hosts or host response to the donor by coadministration of the cells or factors along with foreign substances or tissues to which such immediate tolerance is desired. In addition, and in particular, these cells and/or factors permit the hosts to become tolerant of both present and future grafts where the donor tissue is derived from the same genotype donor as tissue coadministered with the cells or factor.

DISCLOSURE OF THE INVENTION

The invention provides fresh cells and immortalized cell lines capable of secreting factors useful in suppressing the immune response to any desired antigen, and in encouraging engraftment of foreign cells. The immune response may be that of the host against allogeneic tissue (host versus graft) or that of donor immunocompetent cells to the tissues of the host (graft versus host). The formation of chimeras of the recipient shows engraftment has occurred and permits acceptance of future allografts. Other unwanted immune responses which the cells and soluble factor of the invention are capable of suppressing include allergic and autoimmune responses.

Thus, in one aspect, the invention is directed to natural suppressor cells and cell populations containing them, wherein the natural suppressor cells are of two phenotypes. In one phenotype, the "null" phenotype, the surface marker pattern lacks markers characteristic of either B or T cells, as well as macrophage markers. In the "double negative suppressor" (DNS) cell type, the cells lack surface markers characteristic of macrophage and immunoglobulins, and also CD4 and CD8 markers characteristic of helper T cells and cytotoxic T cells, respectively. However, DNS cells are $CD3^+$, $TCR\alpha\beta^+$, and thus contain these specific markers characteristic of T-cell lineages. Both of these suppressor cell types can be expanded and/or cloned and can be used in the form of cell preparations wherein the suppressive effects of the null or DNS cells are not outweighed by accompanying components of the composition such as $CD4^+$ and/or $CD8^+$ lymphocytes. The efficacy of the cell composition as a suppressive reagent can be confirmed by its mixed lymphocyte reaction (MLR) in vitro.

These suppressive cells lines and cell preparations are useful in conjunction with bone marrow and organ transplants in preventing graft-versus-host disease (GVHD) and in encouraging the engraftment of the transplanted allografts so as to result in chimeric recipients. The invention is also directed to method to prepare and expand these cell compositions and cell lines, and to their uses in suppression of the immune response, as well as to pharmaceutical compositions containing them.

In still another aspect, the invention is directed to a population of bone marrow or blood cells which is enriched in progenitor cells and which can be obtained simply by density gradient sorting of mononuclear white blood cells, and to methods to prepare this population. This population, enriched in CD34 surface marker, is thus obtainable by retrieving the white blood cell mononuclear subfraction of the appropriate density.

In another aspect, the invention is directed to a soluble suppressor factor secreted by natural suppressor cells. This factor is useful in various conditions where unwanted immune responses occur. Thus, an additional aspect relates to treating these conditions with the soluble factor of the invention and to pharmaceutical compositions suitable therefor.

In other aspects, the invention is directed to recombinant materials and methods for the production of the soluble factor protein and to antibodies and fragments thereof which are specific for the suppressor factor.

MODES OF CARRYING OUT THE INVENTION

Figure 1:
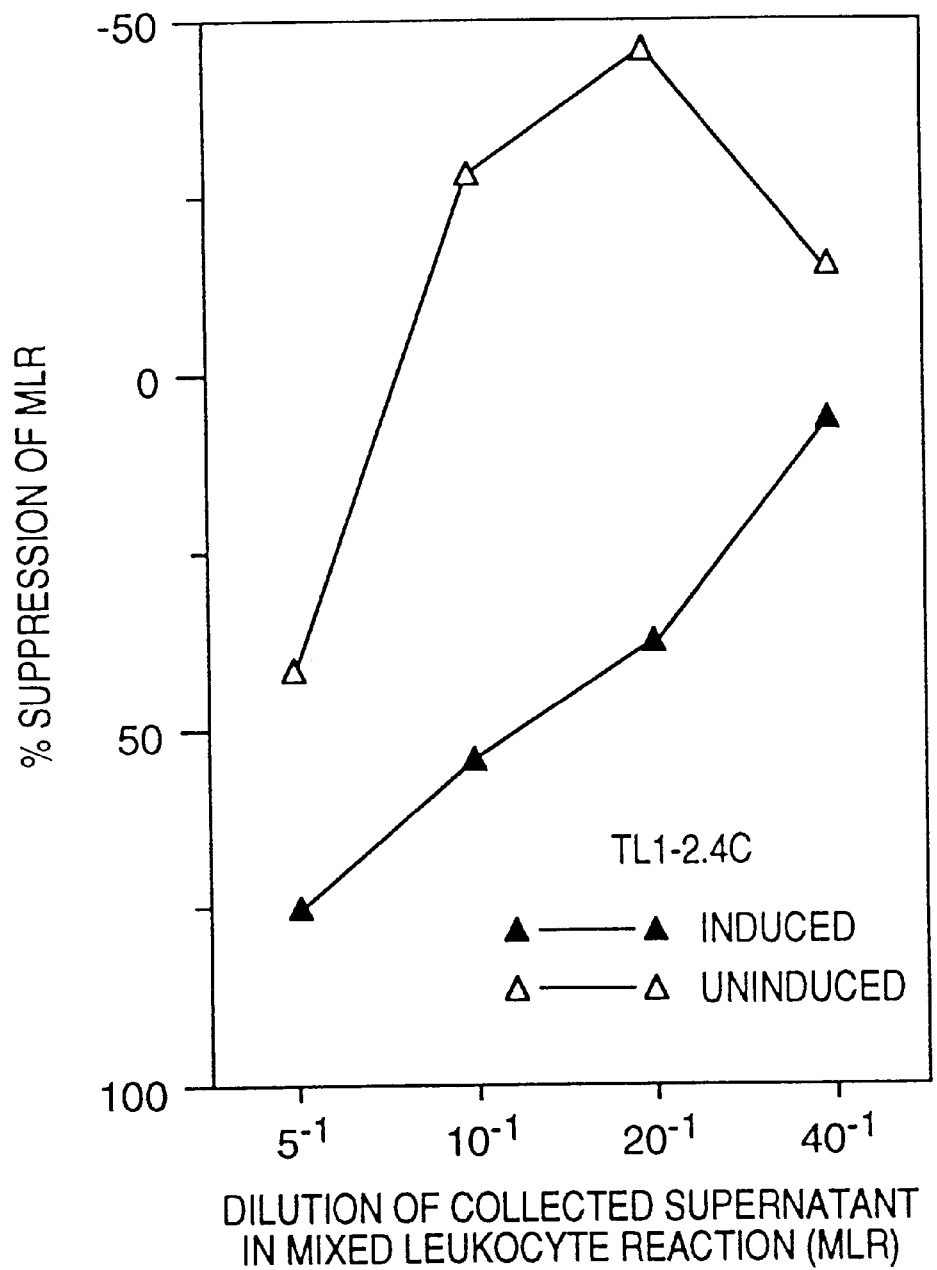
FIG. 1 shows the suppression of MLR by the NS cell supernatants.

The invention is directed to materials and methods capable of immunosuppression in human and other animal subjects. "Immunosuppression" is defined herein as that term is used generally to mean the lowering of an immune response to challenge. While suppression of the response to a particular antigen may be desired, the "suppression" is not so limited. The ability of the soluble factor of the invention to suppress immune response is antigen-independent.

"Specific immunotolerance" refers to a characteristic of a host described as the failure of an immune response to occur when a particular target antigen is encountered by either the host or donor material immunocompetent cells. The target antigen may be for example a simple soluble protein or carbohydrate, an infectious cell, or a cell surface. The donor tissue may be an allogeneic transplant tissue which contains immunocompetent cells, in this case the hosts' own tissue are target antigens.

"Donor material" refers to a material provided to a recipient to which immunotolerance is desired. The nature of the donor material's immunoreactivity on a molecular level may or may not be known; for example, it may be desirable simply to tolerize a host against allogeneic transplants. In this case, the donor material consists of whatever immunogenic and immunocompetent substances are present in the transplanted tissue.

It is desirable to prevent the response of the host cells to donor tissue (host-versus-graft disease) and of graft-versus-host disease. The latter is accomplished by preventing an immune response on the part of a transplant tissue to the tissues of the host. Under such circumstances, the "donor material" comprises immunocompetent cells which respond to whatever antigenic substances are present in the transplant recipient which trigger an immune response by this material.

"Null surface phenotype" refers to the property of one type of the cells of the invention wherein they lack the surface markers characteristic of T cells, B cells, or macrophages, and have morphologies similar to natural killer cells. Thus, they are large granular lymphocytes which lack antigen specificity and carry out their functions without antigenic stimulation. With regard to surface markers, the appropriate surface markers in the murine system include Lyt-1, Lyt-2, and surface immunoglobulins such as murine Ig and Ia. These markers are not present on murine null NS cells. Each mammalian system has its typical corresponding markers, which in the human system includes markers recognized by various monoclonal antibodies known in the art.

In general, generic terminology with regard to surface markers for all vertebrate species will be used; markers typical of T-cell subsets include CD3, CD4, CD8 and CD34; markers typical of immunoglobulins include Ig; markers typical of macrophage include MAC-1. Thus, the null cells derived from any species, including murine and human, are characterized by a phenotype of IL-2R$^+$, Ig$^-$, MAC-1$^-$, CD3$^-$, CD4$^-$, CD8$^-$, TCR$\alpha\beta^-$. "DNS phenotype" refers to double negative suppressor phenotypes wherein the suppressor cells lack CD4 and CD8 markers. They also do not bear markers for B cells or macrophage. However, these cells are CD3$^+$ (and are therefore T cells) and TCR$\alpha\beta^+$. DNS cells from any vertebrate, including murine and human, are characterized as IL-2R$^+$, Ig$^-$, MAC-1$^-$, CD3$^+$, CD4$^-$, CD8$^-$, TCR$\alpha\beta^+$. Since they are suppressor cells, they also suppress the MLR in vitro.

"Corresponding" target cells refers to standard assay cells which cytotoxic lymphocytes would be expected to lyse. In the murine system, these are YAC-1. In the human system they are K562 cells.

"Cell line" or similar words such as "cells", "cell cultures", and the like refer to the specific genotype described, to its progeny, and to mutants and derivatives thereof which retain the essential characteristics of the original cell. It is well understood that naturally occurring or deliberately induced mutations are common in propagation of particular cell lines, many of which are irrelevant to the desired properties. For example, in the cells of the invention, the ability to suppress the mixed lymphocyte reaction must be retained, as well as the characteristic phenotypic surface patterns for either null or DNS cells, as described above. Other metabolic properties, such as nutritional requirements, antibiotic resistance, and the like are irrelevant to the functionality of the cells, and the definition, as it relates to a particular "cell line", includes mutants and derivatives which contain such alterations. In addition, it is understood to be possible to hybridize two cell lines to retain desired characteristics from both partners, eliminating others. Such hybridomas are considered to be derivatives of the original cell line when the required properties are retained.

In the invention herein, a distinction is made between cloned cell lines and freshly prepared cell cultures which are either or both enriched in a desired population having certain specified characteristics and/or depleted in cells or other components with properties that interfere with the suppressive activity of the null and DNS cells. Bone marrow, thymus or splenocytes are suitable sources of freshly prepared null or DNS cells which can be fractionated, as described below, for example, using FICOLL HYPAQUE (sucrose polymer) and/or PERCOLL (colloidal silica) gradients. In addition, these fractions may be enriched for desired cell populations by supplying suitable growth factors to encourage the proliferation of the desired cells. These freshly prepared, enriched but mixed populations are referred to herein as "fresh" cells. These are distinguishable from the specifically cloned cell lines which can be prepared, if desired, from such "fresh" cells and which are, for practical purposes, a homogeneous population of the same genotype and are either null or DNS cells. Such cell lines may be prepared from any vertebrate source, most usefully, from murine and human sources. Similarly, the suppressor factor of the invention may be prepared using cells from any vertebrate subject.

"Suppresses the mixed lymphocyte reaction (MLR)" refers to the ability of the subject material (soluble factors or cells) to prevent the uptake of a marker substance such as thymidine by maturing T cells in the response which occurs when lymphocytes from allogeneic sources are mixed. Specifically, this property may be tested by the procedure specified according to Hertel-Wulff et al., 1984 (supra), incorporated herein by reference (see below). In general, MLR suppression is species-specific—i.e., the MLR assay system should be comprised of cells from the same species as the suppressor cells.

"Simultaneous" administration is meant to be approximately contemporaneous, i.e., within several hours.

Activity in the MLR

The NS cells and NS factor protein of the invention are characterized by, and are useful by virtue of, their in vitro or in vivo activities. Their in vitro activity is demonstrated using the mixed leukocyte reaction (MLR), a commonly used protocol to detect alloreactivity. In this protocol, lymphocytes from two genetically different individuals of a species are mixed in a culture medium. As the cells of each individual bear different major histocompatibility antigens (MHC) on their surfaces, the T cells of each respond to these differences. The measurement of the response can be simplified by irradiating the cells of one species to permit them to behave only as stimulators of an immune response by the unirradiated (responder) cell population. The immune response is presumed to involve initial secretion of lymphokines by the amplified T cells among the responders, which lymphokines mediate the maturation of cytotoxic T responder cells. This proliferation is monitored by uptake of labeled thymidine ($[^3H]TdR$) and suppression of the response is indicated by inhibition of labeled thymidine uptake.

In more detail, in one form of the assay as conducted herein, $5\times10^5$ normal BALB/c spleen responder cells are mixed with $7.5\times10^5$ normal C57BL/Ka stimulator cells which have been irradiated in vitro. After 4 or 5 days, the mixed culture is pulsed with $[^3H]$-thymidine and thymidine uptake measured after 18 hr. Control cultures typically give $110,000\pm7,000$ cpm, and this measure is compared with cpm obtained from cultures to which NS cells or supernatant-containing NS factor had been added, as described below. Both fresh and immortalized DNS and null NS cells, and the soluble factor they secrete, are capable of inhibiting thymidine uptake in the MLR.

Alternatively, the MLR can be measured by assessing the IL-2 secreted into the supernatant. Supernatants are collected and added in serial dilutions to HT-2 cells ($10^4$ cells/well) in flat-bottom microtiter plates. After 24 hours culture at 37° C., proliferation is measured by the tetrazolium assay (MTT assay) described by Mosmann, T., J Immunol Meth (1983) 65:55, or by thymidine incorporation. For thymidine incorporation, 1 $\mu$Ci/well of tritiated TdR (specific activity 6.7 Ci/mmol) is added 4 hours before harvesting the culture on glass filters and the harvested cells are counted in a Beckman Liquid Scintillation Counter. IL-2 concentration is calculated in comparison to titration of standard recombinant IL-2 in the same assay. The ability to inhibit uptake of the thymidine or IL-2 production by responder cells is independent of the antigenic makeup of the stimulator cells and does not require that the haplotypes of the suppressor and responder cells be matched. The mechanism of the suppression is not known, but it has been established that neither IL-2 induced proliferation of HT-2 cells nor IL-1 secretion by macrophages is directly inhibited by the cells or factor of the invention.

Suppression of GVHD

In one assay to assess the in vivo activity for suppression of GVHD, mice which have been irradiated with sublethal dosages of radiation are injected with suspensions of the fresh or cloned NS cells or with the factor, each coadministered with spleen cells or bone marrow derived from an allogeneic species. Subsequent prevention of lethal graft-versus-host disease confirms the immunosuppressive action with respect to the donor cell immune attack on the host. The DNS and null NS cell suspensions and the NS factor proteins are able to suppress the immediate immune response of the immunocompetent donor cells against host tissues.

While the data in these assays show the prevention of graft-versus-host disease—i.e., immunotolerance of donor immunocompetent cells with respect to host tissue, in the case of chimeric hosts it thereby follows that the host's own immunocompetent cells are, in a complementary manner, tolerized to allogeneic or other foreign tissue. In addition, these results demonstrate the ability of the cells and factor to generate immediate immunosuppression.

Assay for Enhancement of Engraftment

For those recipients receiving bone marrow rather than spleen cells, immunotolerance to later skin allografts where the donor was of the strain from which the bone marrow was derived is achieved in the recipients if engraftment has occurred. These direct experimental results demonstrate the ability of the DNS and null NS cells and the NS factor to permit engraftment. The cells to be transplanted can also be assayed for their potential to effect engraftment by assessing the proportion of cells which contain CD34 surface markers. This assessment can be made using standard techniques such as immunofluorescent staining followed by FACS. The methods of the invention described below provide for enrichment of the cell population in cells with these surface markers.

Preparation of NS Cells

Propagation of spleen cells derived from TLI or neonatal mice is conducted as described by Hertel-Wulff et al., 1984 (supra). Mice were used as convenient subjects, but, of course, other vertebrates could also be used.

Human cells are also available as subject cultures using spleens removed for medical indications from neonates or removed from previously ascertained donors who, for other medical indications, had been subject to total lymphoid irradiation, and are recently deceased. In the alternative, human bone marrow which carries null and DNS surface phenotypes can be used. It has been shown by the present applicant that suppressor cell compositions consisting essentially of DNS cells are readily prepared from neonatal spleen, normal adult spleen, adult TLI spleen and bone marrow. Null cells have been prepared from adult TLI spleen and normal thymus.

A variety of separation procedures can be used to obtain the desired cell populations. In general, the cell population is derived from a blood cell source such as bone marrow or blood and represents a low density fraction thereof. The low density fraction, depending on the source, is about less than 10%, preferably less than 5% of the total cells in the blood cell source. The composition of this low density fraction is such that the composition is capable of suppressing the mixed lymphocyte reaction, but preferably is not capable of killing the corresponding target cell population. In order to show these characteristics, this low density fraction must have a ratio of suppressor cells, either or both null NS cells or DNS cells, whose suppressive activity is not outweighed by the immunoactivity of helper and cytotoxic T-cells bearing CD4 and CD8 markers. In addition, this low density fraction may include progenitor cells such as CD34$^+$ cells, or may be supplemented with such progenitor cells. The precise manner of preparing the low density fraction will vary with the source of blood cells and the desired application. However, in general, gradient separation based on cell density is employed. By routine optimization, it is possible to establish precise density gradient fraction limits in g/ml for the desired fraction. The correct characteristics for the isolated fraction may then be established by demonstration of the ability of the fraction to suppress the MLR and, if desired, to fail to show cytotoxicity to corresponding target cells.

For example, isolation of a suppressive cell composition from mouse bone marrow can be conducted by treating a suspension of cells from murine bone marrow with a PERCOLL gradient and obtaining the gradient fractions. Recovery of the low density fraction representing about 5% of the total starting cells represents an effective suppressive composition. Similarly, human bone marrow may be subjected to fractionation using a combination FICOLL HYPAQUE gradient (to remove polymorphonuclear cells), starch treatment to remove red blood cells, plastic adhesion treatment to remove monocytes, and so forth, in conjunction with subjecting the cells suspension to a PERCOLL gradient and recovering the low density fraction containing roughly 5% of the starting material, similarly to the procedure with regard to murine cells. Preparation of these fresh cell compositions from human bone marrow involves a few additional steps designed to deplete certain types of cells from the compositions.

The fresh cells can be more finely sorted by subjecting the suspensions to preliminary fractionation followed by flow cytometric techniques to recover specifically cells which are DNS or null by virtue of their surface markers. In this procedure, the cells are selectively stained with regard to the desired surface features and sorted accordingly.

In one illustrative procedure, if bone marrow is used, the null lymphocyte population can be isolated using standard gradients such as FICOLL HYPAQUE or PERCOLL and cultured in standard tissue culture media with the addition of an appropriate lymphokine such as IL-2 or the supernatant from human peripheral blood lymphocytes stimulated with PHA. The null and DNS phenotypes are propagated as a polyclonal population, and then colonies are analyzed for suppressive activity using a human mixed lymphocyte reaction (MLR) similar to that described for the murine cells herein. The isolated phenotype resembles that described herein for the murine system. In addition to suppressing the appropriate MLR, the cell has a null or DNS surface phenotype and no natural killer function—i.e., it is not able to lyse human tumor K562 cells.

Verification that an appropriate population has been obtained is provided by the ability of the composition prepared to suppress the MLR in vitro. Provided the appropriate enrichment/depletion has occurred in the preparation, and the appropriate phenotype is ascertained, in vitro suppression of the MLR provides a showing that the composition is of sufficient purity to have the desired suppressive effect in vivo.

In addition, the population has reduced or no ability to kill the corresponding target cells, such as YAC-1 for mice or K562 for humans.

In addition to preparing enriched/depleted populations by fractionation, the desired cells can be expanded using cytokines such as IL-2, PHA, or ConA, alone or in combination.

In one typical procedure illustrative of the general approach, wherein the murine system is exemplified, spleens were removed aseptically either from newborn BALB/c mice (1–14 days old) or mice which had been subjected to TLI. In the irradiation procedure, 4–6 month old male BALB/c mice were anesthetized daily with pentobarbital and were positioned in an apparatus designed to irradiate the major lymphoid organs (lymph nodes, spleen, and thymus) described by Slavin et al., *J Exp Med* (1977) 146:34; skull, lungs, tail, and hind legs were shielded. The mice were given 200 rad/day 5 times a week for a total dose of 3,400 rad, using a dose rate of 92 rad/min with a 0.35 mm copper filter and a 52 cm source/axis distance. Tetracycline was added to the drinking water during TLI and for one week after completion of radiation. TLI-treated mice were sacrificed between 1–3 days after completion of TLI.

Single cell suspensions were prepared by incising the capsule and disrupting the splenic parenchyma. The suspended cells were cultured in RPMI-1640 containing 25 Mm HEPES, 2 Mm glutamine, and $5 \times 10^{-5}$ M 2-mercaptoethanol, with 10% fetal calf serum (FCS) and 10% supernatant from Concanavalin A stimulated rat spleen cells (CAS). CAS was prepared as described by Oseroff, A. et al., *J Immunol* (1984) 132:101–110. Aliquots of $1.5 \times 10^6$ cells per well were placed into 24-well plates, and aliquots of $5 \times 10^6$ cells were placed in small flasks. In some cultures $5 \times 10^5$ TLI-treated cells were incubated with $1 \times 10^6$ spleen cells irradiated with 1500 rads in vitro, as feeder cells, and fresh feeder cells were added every 10–14 days for the first 2–3 weeks. Cultures were fed with 10% CAS-containing medium every 2–3 days for the first 2 months, at which time the cultured cells grew slightly adherent to the plastic surface. Cultures were then fed every day and maintained in vitro for at least 48 months. After 8 months in cultures, the cells were cloned using limiting dilution by seeding using 1.5–5 cells per ml in complete medium supplemented with 10% CAS.

The cloned cells were moderately large with granular and vacuolated cytoplasm. These cell lines, one obtained from neonates and designated 4BA4, and two others obtained from TLI mice and designated TLI-C7 and TLI-2.4C were used for further study.

In a completely analogous manner, populations of suppressor cells from other species are stimulated and expanded. Human suppressor cell populations prepared from, for example, spleen, thymus or bone marrow are expanded using similar steps.

Both types of murine NS cells are not able to lyse YAC-1 tumor cells; human NS cells do not lyse K562 cells. However, of course, they suppress [$^3$H]TdR uptake in the MLR.

Enrichment in CD34+ Cells

It has also been found possible to enrich the cell population derived from a mammalian blood cell source for progenitor cells as indicated by the presence of the marker CD34 in humans. An enrichment in such progenitor cells is useful in situations wherein autologous stem cells need to be transplanted into subjects to restore stem cell activity, as well as in allogeneic transplants. For example, patients who have tumors treated by lethal doses of chemotherapy and/or radiation, such as those with breast, ovarian, or myeloma type cancers cannot survive the treatment without restoring their hematopoietic progenitor cell systems. Generally, this is done by administering cells from the patient's own bone marrow. The bone marrow is subjected to treatment to remove the white blood cells and these are frozen. It has also been possible to obtain sufficient progenitor blood cells from the peripheral blood of patients who have been treated with G-CSF. However, while use of blood is more convenient in terms of patient comfort, the number of white blood cells which would include these progenitor cells, as prepared by leukophoresis and required for storage is inconveniently large. Storage is effected in the presence of DMSO, which may not be completely removed. Further, there have been problems with contamination with the patient's tumor cells; the large number of cells stored makes purging impractical.

These problems have been avoided previously by passing the white blood cell preparation obtained from blood over a column containing anti-CD34 antibodies and freezing only the adherent CD34$^+$ cells. However, the columns are not reusable and are costly.

In the method of the invention, a concentrated portion of the blood or bone marrow containing an enriched population of CD34$^+$ cells can be obtained, without the necessity of using an expensive affinity column, by gradient density separation. It has been found that under conditions previously used for gradient separation of human hematopoietic progenitor cells, wherein precautions have not been taken to confine the progenitor cells to a small fraction (<5%) of the total cells subjected to separation and to adjust the ionic strength to that of physiological salt, satisfactory enrichment and yields cannot be obtained. According to the method of the invention, gradients are employed wherein ionic strength corresponding to physiological salt is ensured, and gradients are prepared such that at least 50% of progenitor cells in the original cell population are recovered in a narrow density range which accounts for <5% of cells obtained from the gradient.

In one exemplary approach, rather than the conventional use of 1 part 1× physiological saline to 9 parts PERCOLL to prepare a stock solution for further dilution in physiological salts for gradient formation (even with pH adjustment to physiological pH) gradients obtained by further diluting the stock with RPMI have been unsuccessful in providing fractions enriched in the desired progenitors. According to the method of the invention, a dilution of 1 part 10× physiological saline to 12 parts PERCOLL, with pH adjustment, is one workable embodiment whereby preparation of a stock solution at physiological salinity can be assured. Subsequent dilution of the stock with, for example, 50–60% of a solution corresponding to physiological salt such as RPMI or Ringer's solution in 2.5% discontinuous steps then results in a satisfactory gradient.

The invention method thus results in a gradient separation conducted at the ionic strength and osmolality of physiological salt. The 12:1 ratio of PERCOLL to 10× physiological salt results in a stock which is, itself, at physiological osmolality. This alters the size distribution of cells as compared to prior art conditions, which exceed physiological osmolality.

In a typical preparation, the manufacturer's directions for preparing a gradient are followed, except that the required 12 PERCOLL:1 10× physiological saline dilution with a 10× concentration physiological saline is employed to obtain the stock solution and the pH adjusted to physiological pH. The resulting osmolality of this stock PERCOLL is 280–290 mOms; corresponding to that for humans. According to the typical dilution of 9 parts PERCOLL: 1 part 10× physiological saline ordinarily used to obtain stock, osmolalities of 310–320 mOms are obtained.

With the appropriate dilution of PERCOLL stock, a conventional gradient using 50–60% dilutions of a solution corresponding to physiological salt in 2.5% discontinuous steps and separation according to the gradient results in a satisfactory provision of the required enriched fraction.

In general, the enriched population constitutes the lowest density portion of the gradient representing 5% or less of the cells subjected to the gradient, preferably 3% or less.

However, there is considerable variation from patient to patient, and the fractions should be assessed for surface markers using known techniques. For autologous transplants, it is necessary only to assay the levels of the CD34 marker to assure that a sufficient percentage of the cell population is, in fact, progenitor cells. For allogeneic transplants, however, it is also helpful to assure that the $CD4^+$, $CD8^+$ population is sufficiently depleted that graft-versus-host disease does not occur. In some instances, even though the fraction which resides in the 45–47.5% PERCOLL gradient illustrated below often contains substantial amounts of $CD34^+$, the T-cell population may trail into this fraction and make it undesirable for use in allogeneic transplants. In autologous transplants it is clearly undesirable to deplete the T-cell component completely, since the graft-versus-leukemia response and engraftment will be inhibited. In allogeneic transplants, the necessity for these cells remains, but the presence of the suppressor cell populations of the invention in these fractions offsets the ability of these T-cells to mediate graft-versus-host disease.

The density gradient is generally conducted on cells that have been depleted of red blood cells and/or polymorphonuclear cells. Thus, cells from blood or bone marrow are first subjected to sedimentation in heta-starch solution to remove red blood cells and a FICOLL gradient for removal of polymorphonuclear cells prior to subjecting them to the PERCOLL gradient. Alternative methods for this removal comprise centrifugation to remove red cells. The cells are then subjected to PERCOLL gradients and the hematopoietic progenitor cells are enriched 10–20 fold in the fractions of 40–45% PERCOLL; the total number of cells in these fractions represents only about 5% of the original cells in the blood cell source and in general, at least 50% of the original hematopoietic progenitor cells ($CD34^+$) can be recovered.

The recovered fractions can be assessed for a satisfactory population of progenitor cells by determining the presence or absence of the CD34 marker. Typically, at least 10% of the cells in the recovered fraction, preferably 15%, and more preferably 20% will bear the $CD34^+$ marker.

The recovered fraction can then be stored and used for stem cell replacement in subjects requiring this treatment.

Preparation of the Soluble Factor

The suppressor cell lines of the invention can generally be derived and cultured as described above. They can be further immortalized by fusion to immortalizing cell lines, infection with virus, or other means known in the art.

The soluble factor is produced from the expanded, immortalized or cloned cells by suitable inducing conditions, which include those particular conditions specified above, as well as addition of other materials which stimulate the phosphatidyl inositol pathway to the medium. The supernatants containing NS cell-secreted factor may be used per se, or may be subjected to purification techniques as described below to isolate the factor with the suppressor activity by tracking active fractions as measured by suppression of the MLR.

Thus, the suppressor cells of the null or DNS phenotypes may be induced to produce the soluble suppressor factor by addition of suitable inducing agents. One effective class of such agents includes those which activate the phosphatidyl inositol pathway, such as the phorbol esters. For example, secretion of the NS factor is stimulated by the addition of 5–20 ng/ml of PMA and 0.05–1.0 $\mu$g/ml of a calcium ionophore to the medium.

Similar conditions are used to stimulate suppressor factor production from any mammalian cell cultures, including human.

The suppressor factor from the murine cells exemplified has been partially characterized. The analogous factor from cells of other mammalian species, including humans, has similar properties. First, it has been verified that the supernatants of the isolated cell lines are free of activity exhibited by IL-1, IL-2, IL-4, IL-6, IL-7, and IL-10. The supernatants do contain IL-3, GM-CSF tumor necrosis factor-$\alpha$ (TNF$\alpha$), TGF-$\beta$, and $\gamma$-interferon activity. However, the suppressor factor has been shown not to be identical to these. With respect to IL-3, recombinant IL-3 does not show suppressive activity in the standard MLR. Recombinant $\gamma$-interferon does not show such activity when IL-2 secretion is used as a measure of MLR. After removal of all $\gamma$-interferon from the supernatant by immunoaffinity chromatography, the suppressive activity of the supernatants is retained.

Initial chromatographic separation on SEPHADEX (dextrose beads) G-150 of the proteins from the media in which the cells were cultured showed 90% of the suppressor activity in the two peaks of 135 kd and 240 kd. These peaks are removed from the peaks associated with elution of the major proteins in the media. In an exemplary procedure, 650 $\mu$l of the supernatant is loaded onto a SEPHADEX G-150 column and eluted in pyridine:acetic acid buffer or PBS buffer at pH 7.2. The eluate is collected in 500 $\mu$l aliquots using size markers.

The specific activity of the pure suppressor factor is high, as the protein profiles on the SEPHADEX column appear identical for induced and noninduced cells; however, only the 135 kd and 240 kd peaks from the induced cultures show suppressive activity. These peaks are believed to represent multimers of the SF of the invention.

The partial purification of the suppressor factor (SF) from the TCI-C7 line is described in Example 3 hereinbelow. Briefly, the supernatant is first concentrated and then chromatographed on a DEAE-Sepharose column and eluted in a sodium chloride gradient. The fractions containing the MLR suppressing activity are pooled, concentrated and dialyzed and further purified on a lentil lectin column. A lentil lectin Sepharose 4B column may conveniently be used and the dialyzed fractions are applied in buffer at pH 8.0. The column is eluted with a linear gradient of a carbohydrate known to bind said lectin, preferably $\alpha$-methyl-D-mannoside. The fractions assayed to suppress the MLR are then pooled and subjected to electrophoresis under nonreducing conditions using SDS-PAGE. An approximately 20 kd band is detected by silver staining and the corresponding position is eluted and the recovered protein is able to suppress the MLR. Alternatively, the fractions from the lentil lectin column which exhibit activity can be sequenced directly. The N-terminal sequence (SEQ. ID NO:7) of the eluted protein is: X-Glu-Asn-Val-Gly-Leu-Asn-Glu-Val-Val-(Ala/Phe)-Leu-(Lys/Leu)-Tyr-Gln-Val. The amino acid at position 1 could not be determined definitively.

Antibodies are raised to the peptides (SEQ. ID NO:2) Leu-Asn-Glu-Val-Val-Ala-Leu-(Lys/Leu)-Tyr-Gln-Val by immunization protocols in suitable mammalian hosts, typically rabbits. The antisera obtained are able to remove the suppressive effect of the supernatant from PMA/ionophore-stimulated supernatants of TLI-C7 cells in the MLR after solid-phase immunoadsorption. Further, these antibodies immunoreact with the 20 kd band on the SDS gel.

The antibody preparation is then conjugated to a solid support and can be used for affinity purification of SF from the stimulated supernatants.

Recombinant Production of the Suppressor Factor Protein

The suppressor factor protein of the invention may be isolated from cells or cell lines after appropriate stimulation with PMA/ionophore or may be produced using recombinant means from a variety of hosts. The N-terminal amino acid sequence set forth above is used to design suitable probes for recovery of DNA encoding the SF protein from DNA libraries. Suitable DNA libraries may be prepared from genomic DNA, or, more preferably, as cDNA libraries by reverse transcription of mRNA isolated after stimulation with PMA/ionophore from cells or cell lines capable of secreting said SF protein. The library of choice is then probed using standard hybridization conditions with the degenerate probe mixture designed based on the amino acid sequence set forth above. Alternatively, expression libraries may be prepared using, for example, $\lambda$gt11 in *E. coli* and the protein produced by transformants containing DNA encoding the SF detected by immunoreactivity with antibodies which have been prepared by immunizing subjects with the SF or peptide fragments thereof and recovering the antisera.

The encoding DNA is then sequenced to confirm its correspondence to the SF amino acid sequence and ligated into an expression system for transformation into a suitable host. The recovered DNA is also used as a probe to recover the DNA encoding the corresponding SF protein from libraries prepared from other mammalian species, such as the human SF.

A wide variety of expression systems applicable to both procaryotic and eucaryotic hosts is now available, some expression systems, indeed, being available commercially. Thus, suitable expression systems are available for production in *E. coli* or other prokaryotes, in yeast, in insect cells based on a baculovirus expression system, in mammalian cells, and in plant cells. The choice of appropriate host will depend on the desired form of the SF protein as determined by the posttranslational processing capabilities of the cells selected.

The transformed host cells are then cultured under conditions which favor the expression of the encoding DNA, and the SF protein is recovered from the culture. The expression system may be designed so as to effect the secretion of the SF; in this circumstance, the SF is purified directly from the supernatant. Alternatively, the SF may be produced intracellularly, in which circumstance lysing of the cells is required prior to protein purification. The protein is then purified using standard methods such as gel filtration, chromatography, adsorption chromatography, SDS-PAGE, and the like.

The recombinantly produced SF is advantageous in that it can be provided free of any danger of contaminating infectious agents and the level of production can be controlled and elevated relative to cellular proteins so that the purification of the SF is simplified.

Preparation of Anti-SF Antibodies

The SF protein of the invention may be used in standard immunization protocols to generate antisera containing antibodies specifically immunoreactive therewith, and peripheral blood cells and splenocytes which may be immortalized to provide sources for monoclonal antibodies immunoreactive with the SF. The SF, or a selected peptide fragment thereof, is administered under standard immunization protocols and adjuvant regimens to suitable hosts such as rabbits, rats, mice and the like. The antisera or antibody-producing cells are recovered using standard techniques. The antibodies thus obtained are useful in assay systems to determine the presence or level of SF in biological fluids.

Administration and Use

The NS cells either null or DNS and induced supernatants as well as the SF protein per se of the invention will be useful in conferring immunosuppression and immunotolerance on a host subject. Subjects susceptible to this treatment include any vertebrate species, including human, but particularly the NS cells and SF protein compositions are adaptable to use in mammals. The conferred immunosuppression or immunotolerance is especially useful in permitting the host to accept simultaneous or future transplants of tissues or cells from an allogeneic donor. Also, since the suppression is not antigen-specific, subjects with unwanted immune responses to allergens or autoantigens will benefit from administration of the cells or SF protein. Thus, for example, these medicaments are useful to treat autoimmune diseases such as rheumatoid arthritis or myasthenia gravis.

The dosage levels required are highly dependent on the nature of the host and on the nature of the immunological challenge. However, as an overall estimate, in the method of the invention, the NS cells are administered to the host receiving autologous donor material will be in the amount of approximately $10^8$–$10^{10}$ cells/kg of host weight, along with a comparable number of cells to be used in the allogeneic transplant. The amount of SF protein administered is comparable, i.e., the amount produced in the supernatant from about this same number of induced cells. Coadministration with similar numbers of foreign immunocompetent cells permits contemporaneous acceptance of these transplants.

In addition, the foregoing treatment may be used in conjunction with subsequent implantation or injection of tissue from the same donor which has been co-injected with the NS cells or the protein factor, as above. The initial simultaneous administration may use immunocompetent donor tissue, or donor bone marrow or the bone marrow hematopoietic stem cells.

For allogenic transplants, the suppressor cells are preferably derived from the donor in the case of bone marrow transplants, and from the recipient in the case of organ transplants. For use in treatment of autoimmune disorders, the patient is used as the source of the suppressor cells.

The cell populations of the invention which are enriched in CD34+ stem cells are useful both in allogenic and autologous transplantation protocols. While in autologous transplantation suppressor functionality is not required, capability to engraft is extremely important. Thus, the cell populations obtained by the method of the invention which have high populations of CD34+ cells as compared to unsorted populations are helpful in encouraging the success of the transplant both in allogenic and autologous protocols. The source of the stem cells is generally bone marrow although blood can be used provided the subject has been treated with stimulating factors such as G-CSF to enrich the blood in these cells. Treatment with G-CSF, for example, often results in a tenfold enrichment of hematopietic progenitor cells in the blood. The enriched progenitor cell population obtained by density gradient sorting under suitable physiological conditions as described herein can be stored as a subfraction of the blood or bone marrow until needed for subsequent use.

With respect to the cell populations used in connection with transplantation, techniques for administration of these cells as portions of the transplant are well understood by the practitioners of the transplantation art. A variety of techniques using straight forward medical procedures is available.

With respect to treatment for immune suppression per se, administration is typically by injection, either intravenous (especially for the soluble factor) or intraperitoneal (which is preferred for the NS cells). However, other modes of administration, such as oral, transmucosal, or using other formulations as is understood by those in the art may also be used.

Pharmaceutical compositions of SF may be prepared using standard formulation techniques suitable for the mode of administration. Suitable formulations may be found, for example, in *Remington's Pharmaceutical Sciences*, latest edition, Mack Publishing Company, Easton, Pa. In general, the SF active ingredient is supplied at 0.5%–90% of the formulation and suitable excipients, such as buffers, stabilizers, carriers and the like are added. For particular routes of administration, excipients with additional functionalities such as penetrants or detergents may be required.

Suitable subjects for administration of the SF protein of the invention include vertebrates, in particular mammals, including humans in need of immunosuppression. In general, such individuals include those afflicted with autoimmune conditions such as rheumatoid arthritis, myasthenia gravis, juvenile diabetes, lupus erythematosus, multiple sclerosis, and the like. Another major group of suitable recipients includes those with hyperimmune responses to allergens. Still another group includes those who are recipients of transplanted tissues such as kidneys, lungs, heart, bone marrow, skin, and the like.

The subject matter of the invention further includes antibodies immunoreactive with the suppressor factor of the invention. These antibodies are useful in assessing the amounts of suppressor factor present in a biological fluid. Such assessment can be made by standard immunoassay procedures as is well known in the art. Thus, both direct and competitive immunoassays may be used; the antibodies may be labeled, conjugated to solid support, or otherwise modified to render their use in these methods more convenient. Variations on immunoassay protocols suitable for use in the present invention are well known in the art.

The following examples are intended to illustrate but not to limit the invention.

EXAMPLE 1

Suppression of MLR by Cloned NS Cells and Supernatants

Both the NS cells and their induced supernatants were capable of suppressing the MLR conducted as follows: Responder cells ($5 \times 10^5$) and stimulator cells ($7.5 \times 10^5$) were incubated with graded numbers of the NS cells in 0.3 ml/wells in 96-well microculture plates. The culture medium was supplemented with 2 mM glutamine, $5 \times 10^{-5}$ M 2-mercaptoethanol, 100 units/ml penicillin, 100 µg/ml streptomycin, and 10% pooled human serum (VSP, Biocell Laboratories, Carson, Calif.). The NS cells and stimulator cells were given 3300 rad before incubation. Cultures were maintained at 37° C. in 5% $CO_2$ for 5–6 days. Eighteen hr before termination, 1/µCi of [$^3$H]TDR (6.7 Ci/mM) was added to each culture. Cells were harvested with a semiautomatic cell harvester and counted in a Beckmann liquid scintillation counter.

Three illustrative cell lines cultured from the spleens of TLI mice, designated TLI-2.B7 (DNS), TLI-2.H5 (null), and TLI-2.4C (DNS), suppressed the MLR significantly at co-cultured cell counts of $2 \times 10^4$ per well. Suppression in the range of 90% was obtained at this concentration when C57BL/Ka stimulator and BALB/c responder cells were used. Similar results were obtained with A/J responder and C57BL/Ka stimulator cell lines.

Suppression of the mixed lymphocyte reaction was also obtained when supernatant from TLI-2.4C (DNS) cells was added to the cultures (controls give 110,000±7,000 cpm). FIG. 1 shows the data obtained in the MLR comparing the result for added supernatant with and without induction.

Supernatants were obtained from cloned TLI-2.4C cells 24 hr after they had been induced with 10 ng/ml PMA (4-phorbol-12-myristate-13-acetate) and 0.26 µg/ml A23187 calcium ionophore for 4 hr at 37° C./5% $CO_2$. When dilutions of this induced supernatant were added to the MLR, a 75% suppression of the MLR was obtained using a 1:5 dilution of the supernatant. Uninduced supernatant gave only a 40% suppression at this dilution. The results are more clearly seen at a 1:10 dilution, where the induced supernatant gives a suppression of 55% while uninduced supernatant shows a 30% stimulation of the reaction.

The activity of the induced supernatant is destroyed by pronase treatment and is associated with a dialysate of >20 kd.

EXAMPLE 2

Effect of Supernatants from Cloned Activated NS Cells on IL-2 Production

The supernatants were obtained from the TLI-C7 (DNS) clone derived from the spleen of an adult TLI mouse (given total lymphoid radiation), as described by Hertel-Wulff, B., et al., *J Immunol* (1984) 133:2791 (supra). The clone has been verified to have the surface phenotype $CD3^+$, $CD4^-$, $CD8^-$, $TCR\alpha\beta^+$ as set forth by Strober, S., et al., *J Immunol* (1989) 143:1118. The stimulation of these cells with PMA and A23187 was as described by Strober, S., et al., *J Immunol* (1987) 138:699. Briefly, the TLI-C7 cells were grown to confluence in T-75 flasks and PMA (10 ng/ml) and A23187 (0.26 μg/ml) dissolved in RPMI-1640 supplemented with 10% heat-inactivated FCS, was added to the TLI-C7 cells in a final volume of 20 ml/flask. After incubation for 4 hours, the cells were washed 5× with PBS and overlaid with RPMI-1640 containing no additional proteins. The supernatants, referred to later in this example as IC7, were collected 24 hours later and kept frozen at minus 40° C. until use. PMSF was added to the stored IC7 to a concentration of 0.1 mM to prevent protease degradation.

The mixed lymphocyte reaction (MLR) was conducted as described above, except that in lieu of thymidine uptake, IL-2 production was measured as described hereinabove. The results are shown in FIG. 2A. In a control reaction, when responder cells were used alone, no IL-2 was secreted (open circles). When the standard MLR is conducted with the addition of the stimulator splenocytes, IL-2 production reaches a peak of 6 IU/ml after 96 hours (open squares). However, in the presence of a 1/5 final dilution of IC7, suppression of IL-2 secretion is clearly shown, reaching a maximum of only 1 U/ml after 72 hours and decreasing thereafter (open triangles).

It has been reported previously that TLI-C7 cells stimulated with PMA and A23187 secrete TGF-β, GM-CSF, TNF-α, and IL-3, but not IL-1, IL-2, IL-4, IL-6, IL-7 or IL-10 (Van Vlasselaer, P., et al., *Cell Immunol* (in press), incorporated herein by reference). The cytokines whose secretion had been demonstrated were added to the standard MLR assay in concentrations ranging from 1000 to 0.5 U/ml (IFN-γ, IL-3, GN-CSF, TNF-α) or 10 to 0.05 ng/ml for acidified TGF-β. The concentrations reflect the level at which the cytokines were detected in IC7. IL-2 concentrations in the MLR supernatant were measured after 96 hours of culture, and IFN-γ, IL-3, and GN-CSF did not induce significant suppression of IL-2 production. TNF-α and TGF-β did suppress IL-2 production in the MLR but the addition of anti-TNF-α and anti-TNFβ antibodies does not affect the apparent suppressive activity of these factors; therefore, it does not appear that the suppression is in fact due to these factors.

The ability of the IC7 supernatants to suppress IL-2 production from T cells stimulated by mitogens or antibodies was also tested. In these assays, BALB/c splenocytes ($5 \times 10^5$/well) were cultured for 72 hours under conditions identical to those for the MLR in the presence of either ConA (2 μg/ml), PHA (4 μg/ml) or anti-CD3 monoclonal antibody (final 1/200 dilution of hybridoma cell culture supernatant) added to the splenocytes from the start of the assay. Again, the effect of a 1/5 final dilution of IC7 was tested on IL-2 production measured as described above.

Figure 2B:
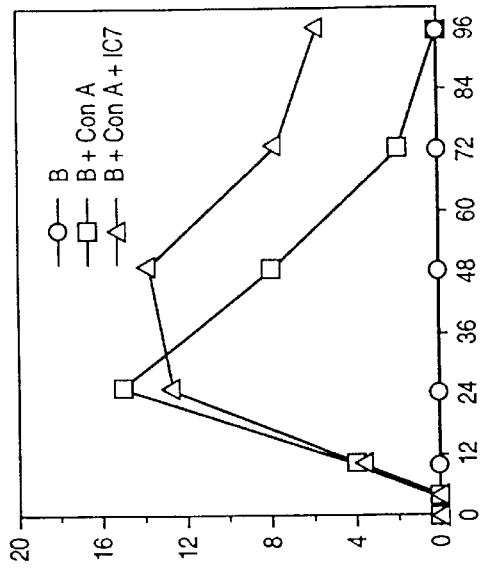
FIGS. 2A–2D show the effect of the stimulated supernatants from TLI-C7 cells on T cell proliferation in the context of MLR and of ConA, PHA and anti-$CD3^+$ treatment, respectively.
Figure 2D:
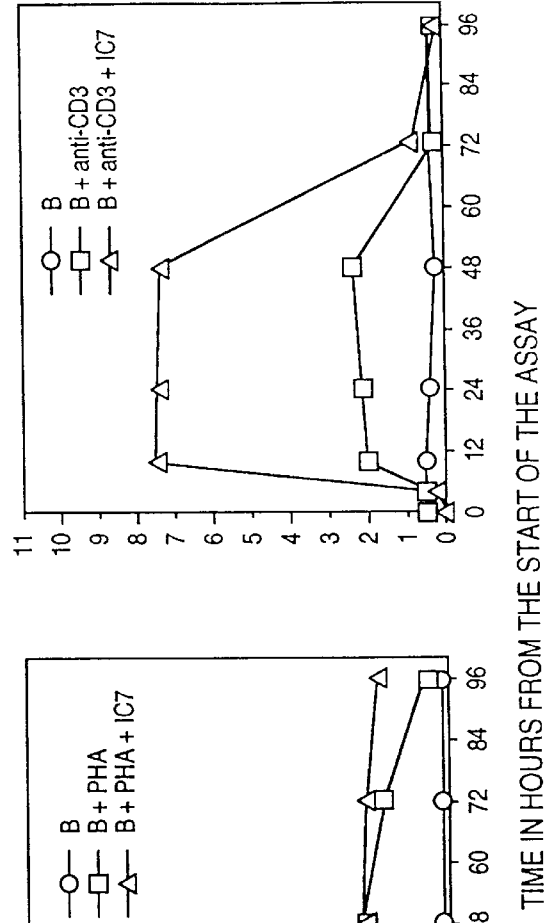
Figure 2A:
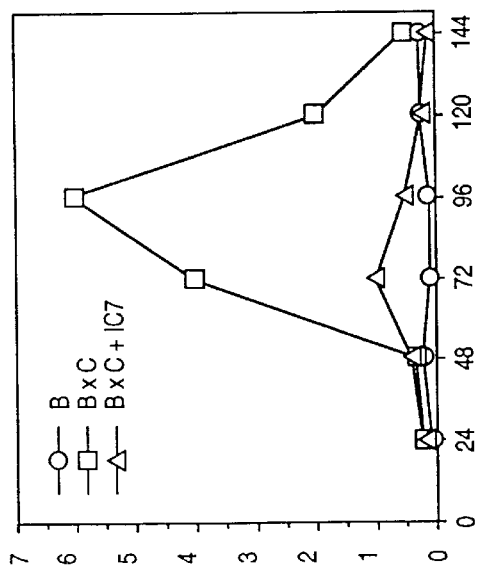
Figure 2C:
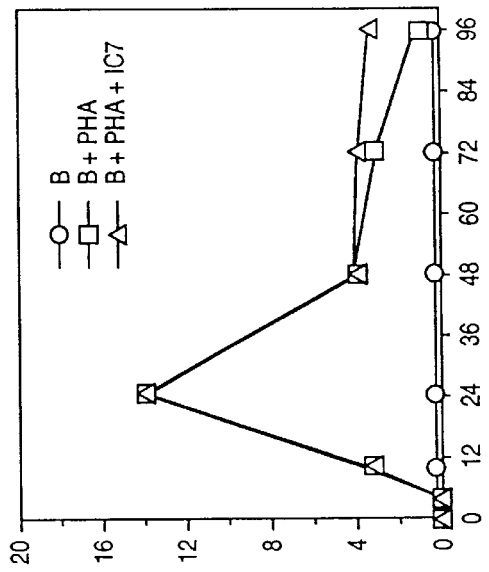

The results are shown in FIGS. 2B–2D. As shown in FIG. 2B, controls without ConA show no IL-2 production (open circles), but splenocytes stimulated with ConA (open squares) show a peak production of IL-2 of 16 U/ml after 24 hours. Addition of IC7 does not appreciably affect this production (open triangles). Similar results were obtained using PHA as a stimulant (FIG. 4C). As shown in FIG. 4D, some enhancement of IL-2 production induced by anti-CD3 stimulation is found; splenocytes stimulated with anti-CD3 produce about 2 U/ml IL-2 after about 6 hours and maintain this level until about 60 hours (open triangles). Addition of IC7 at a 1/5 dilution raises the IL-2 secretion to about 8 U/ml over the same time period.

EXAMPLE 3

Purification and Characterization of NSF

A 2:1 pool of IC7 was incubated with 7 mg/ml silicic acid in PBS for 4 hours at 4° C. under continuous stirring. The silicic acid was spun down and nonadsorbed material was collected and concentrated in a Centricell filtration unit with an NW cut-off of 10 kd.

The resulting supernatant was dialyzed against 20 mM Tris-HCl, pH 8.0, supplemented with 1 mM PMSF, and run on a DEAE Sepharose column at 4° C. using the same buffer. The column was washed with 2 bed volumes of starting buffer and the adsorbed material was eluted at a flow rate of 0.35 ml/min with linear gradient (0–1 M) of NaCl, 20 mM Tris-HCl, pH 8. Fractions of 1 ml were collected and stored at 4° C. until tested in the MLR at a final dilution of 1/5. MLR supernatants were collected after 72 hours and screened for IL-2 content in the HT-2 assay using thymidine incorporation.

Figure 3:
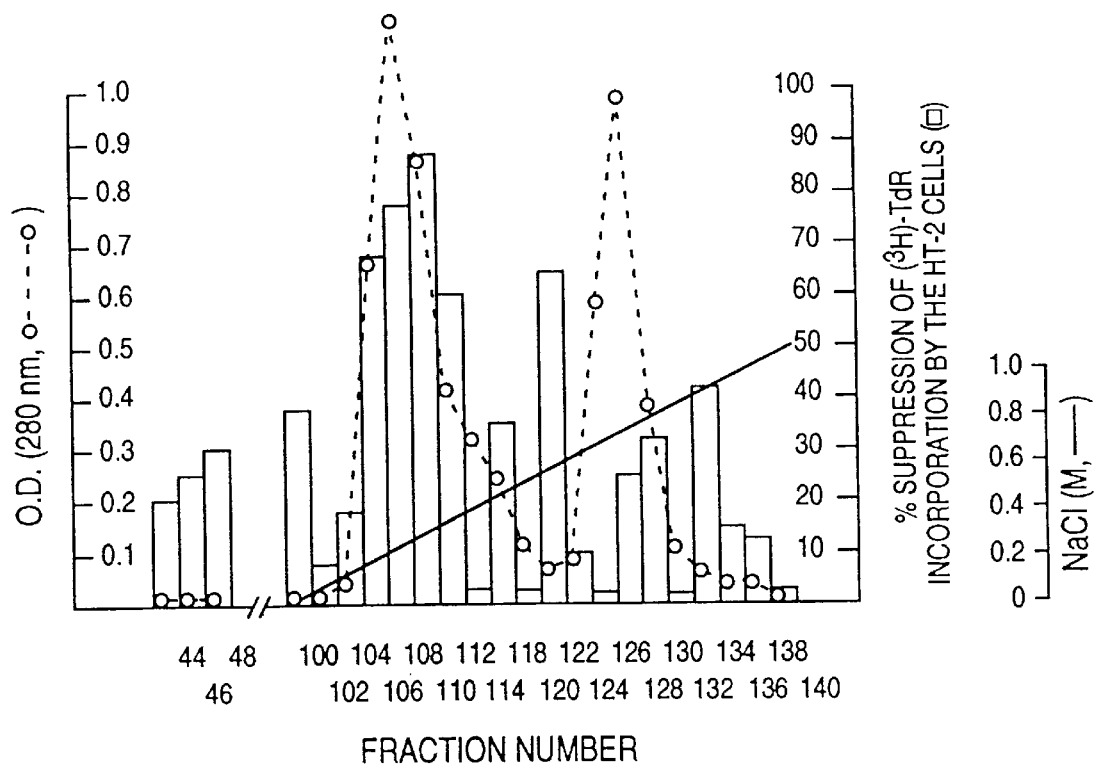
FIG. 3 shows the elution pattern for the soluble factor of the invention from DEAE sepharose.

The elution pattern is shown in FIG. 3. Measurement of protein content at 280 nm shows two major peaks. However, the majority of the MLR suppressor activity elutes between 0.2 and 0.4 M NaCl. The material in fractions 106–112, as shown in FIG. 3, was pooled, concentrated and dialyzed against PBS. This active material blocked IL-2 production in MLR up to a 1/32 dilution.

Characterization of the purified factor (SF) showed that the activity was lost when SF was acidified to pH 2 for 12 hours, boiled for 5 minutes, or protease-treated by incubating the dialyzates for 4 hours at 37° C. with protease immobilized to agarose beads.

Further characterization of the nature of the activity of SF was conducted on this purified factor. In one study, a 1/5 final dilution was added to the MLR at various time points, the supernatants were collected after 72 hours, and IL-2 production measured in the MTT assay. SF suppresses IL-2 production when added within the first 60 hours of the MLR, but when added later, at 66 hours, suppression is no longer shown. Further, in general, effectiveness of suppression diminished the later the SF was added to the reaction.

The effect of SF on APC was also determined by measuring IL-2 production by a T-cell hybridoma stimulated with antigen and Class II-matched APC. $IE^{K+}$ 1G18-LA cell line, which is a cloned macrophage line from thymus, was incubated at day 0 with graded concentrations of IFN-γ (100–0.5 U/ml) for 24 hours. The cells were washed and added to ovalbumin-specific and $IE^K$-restricted T-cell hybridoma line 3DO-18.3. The mixture was cultured for another 24 hours in the presence of ovalbumin, and at the end of the culture period, supernatants were collected and screened for IL-2 content. The SF was added at 1/5 final dilution either to the culture of APC alone or APC plus hybridoma.

Figure 4:
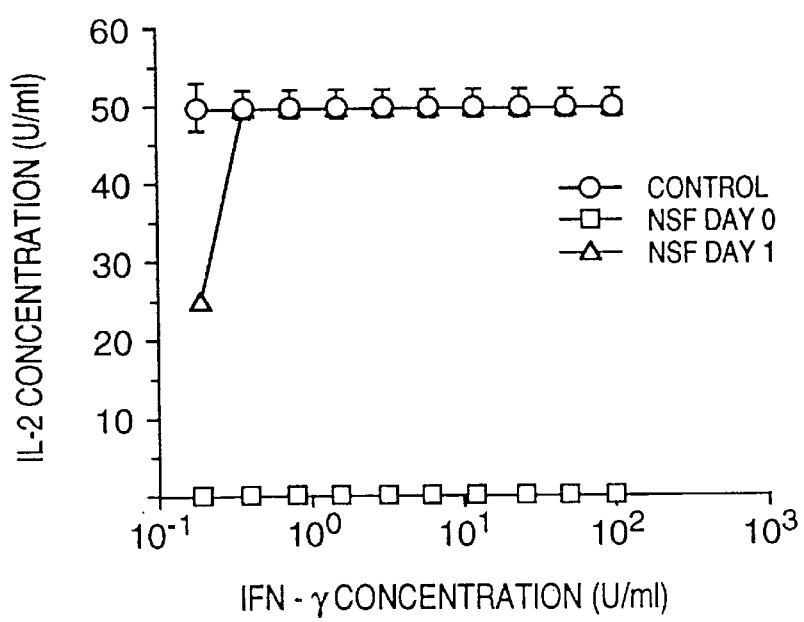
FIG. 4 shows the effect of purified soluble factor on APCs treated with IFN-γ.

The results are shown in FIG. 4 as a function of IFN-γ concentration. As shown, APCs were incubated at day 0 with different IFN-γ concentrations, at day 1 the APC cultures were washed and T cells added together with antigen, and at day 2 the supernatants were tested for IL-2 in the MTT assay. SF was able to suppress the production of IL-2 only when added at day 0 (open squares), not when added after the hybridoma had been included (open triangles), except at the lowest IFN-γ concentration. Controls are shown as open circles.

In an alternate system using $IE^D$-restricted sperm whale myoglobin-specific A.2.1DH1A T cell hybridomas with $IE^{D+}$ A20B lymphoma cells in the presence of horse myoglobin or sperm whale myoglobin 110–121 peptide, similar but not identical results were obtained. In this case, suppression was shown whether or not the APCs were preincubated with SF.

EXAMPLE 4

Effect of Cloned NS Cells on Thymocytes In Vitro

The cloned $TCR\alpha\beta^+$, $CD3^+$, $CD4^-$, $CD8^-$ NS cells represented by TLI-C7, rather than suppressing thymocyte proliferation in response to PHA, in fact stimulate this proliferation. The experiments demonstrating this capability of the cloned NS cells is described in detail by Van Vlasselaer, P., et al., *Cell Immunol* (1991) 136:1–15, the disclosure of which is incorporated herein by reference. However, these cloned cells suppress the MLR, as described previously.

EXAMPLE 5

Correspondence of Fresh Mouse Bone Marrow Cells with Cloned Mouse Bone Marrow Cells Fresh mouse bone marrow cells were subjected to Percoll density gradient separation. Low density cells were separated by flow cytometry, and a DNS population was obtained. The latter cells were shown to suppress the MLR by about 70% when $10^5$ cells were added. Thus, both fresh and cloned DNS cells suppress the MLR.

EXAMPLE 6

Preparation of Fresh Human Bone Marrow Suppressor Cells Enriched for Stem Cells Bone marrow was obtained from normal adult donors for allogeneic bone marrow transplantation after informed consent had been given according to guidelines established by the Stanford Committee for Human Subjects. Human bone marrow cells were either aspirated or taken from cores of bone marrow removed from the iliac crest. Single cell suspensions were separated using Ficoll-Hypaque gradients (Lymphoprep; Nycomed AS, Oslo, Norway). These gradients were subsequently referred to as FICOLL gradients. The mononuclear fraction from this gradient is recovered. The recovered cells were depleted of monocytes by incubation twice on plastic petri dishes for 45 minutes at 37° C. Medium for incubation consisted of RPMI-1640 (Applied Scientific, San Francisco, Calif.), 10% fetal calf serum (HyClone, Logan, Utah), 2 mM L-glutamine, 100 U/ml penicillin, 100 μg/ml streptomycin and 50 μM 2-mercaptoethanol (ME). (Bone marrow cells obtained from the FICOLL gradients were further depleted of myeloid and erythroid cells in some experiments in order to enrich for lymphocytes.) FICOLL-purified buoyant mononuclear cells were washed and incubated with phycoerythrin-conjugated mouse monoclonal antibodies directed against human CD33 (Leu-M9; clone P67.6) (Becton-Dickinson, Mountain View, Calif.) and with mouse monoclonal antibodies to human glycophorin A (gift of J. Griffin, Dana Farber Cancer Center, Boston, Mass.) at 4° C. for 30 minutes. These steps were omitted in later experiments, as they were included in the initial determinations only to simplify the assay procedures on the separated cells. To remove excess antibody, the incubation mixture was layered on a 1 ml cushion of calf serum and centrifuged at 250 ×g for 10 minutes. The pellet was resuspended in phosphate-buffered saline (PBS) containing sheep antimouse antibody coupled to magnetic particles (Dynal, Inc., Great Neck, N.Y.) and incubated as before. Cells were put on a magnetic particle concentrator (Dynal, Inc.) for 5 minutes. Nonbound cells were removed and washed twice. In some cases, mouse monoclonal antibodies directed against CD11b (Mo-1) (gift of J. Griffin) and against glycophorin A were used to remove myeloid and erythroid cells by "panning," as has been described by Greenberg, P.L., et al., *Blood* (1985) 65:190–197.

PERCOLL gradients were prepared using 2.5% or 5% steps ranging from either 40–50% PERCOLL or 45–55% PERCOLL (Pharmacia LKB Biotechnology, Uppsala, Sweden). The stock PERCOLL was prepared according to the manufacturers instructions except that when the stock was prepared, 12 parts PERCOLL to 1 part 10× physiological saline was used (as opposed to 9 parts PERCOLL:1 part 10× physiological saline). The stock solution prepared in this manner has an osmolality in the range of human blood of about 280–290 mOms. The dilution of stock solution to the desired percentage PERCOLL gradients using RPMI then created the gradients for separation; these gradients were also, therefore, maintained at physiological osmolality. Before use, gradients were checked for pH, osmolality and exact density by refractometry (C. Zeiss refractometer).

The FICOLL purified, plastic nonadherent or lymphocyte-enriched marrow cells were mixed with the lowest density PERCOLL, placed on top of the discontinuous PERCOLL gradient, and centrifuged (550×g) for 30 minutes at 20° C. Cells at each interface were collected and washed before testing in the MLR or in the hematopoietic progenitor assays.

The results of one determination using 5% steps ranging from 45–55% PERCOLL are shown in Table IA.

TABLE IA

Yield and Subsets of Marrow Cells After Fractionation

| Marrow Cell Population | Percentage Yield[a] | Percentage of Cells Expressing Surface Marker | | | |
|---|---|---|---|---|---|
| | | $CD3^+$ | $CD4^+$ | $CD8^+$ | $CD16^{+b}$ |
| Unfractionated FICOLL-HYPAQUE Plastic: | 100 52 ± 11 | 17 ± 10 | 9 ± 3 | 9 ± 3 | ND[c] |
| Nonadherent PERCOLL Fractions: | 34 ± 7 | 20 ± 14 | 10 ± 6 | 10 ± 2 | 17 |
| FR.1 (<45%) | 0.9 ± 0.7 | 6 ± 5 | 2 ± 1 | 2 ± 1 | 18 |
| FR.2 (45–50%) | 4 ± 4 | 11 ± 10 | 5 ± 3 | 5 ± 2 | 21 |
| FR.3 (50–55%) | 7 ± 4 | 20 ± 14 | 10 ± 5 | 8 ± 4 | 2 |
| FR.4 (>55%) | 8 ± 6 | 33 ± 24 | 15 ± 6 | 15 ± 6 | 4 |

[a]Mean percent yield ± SEM as compared to the number of unfractionated marrow cells in four experiments.
[b]Average percentage of $CD16^+$ cells in two experiments which were separate from those with other markers.
[c]ND, not done.

Low density PERCOLL fractions 1 (<45% Percoll) and 2 (45–50% PERCOLL) yielded a mean of 0.9% and 4% of the original bone marrow samples, respectively (Table IA). This represents 3% and 11% of the plastic nonadherent cells. High density PERCOLL fractions 3 (50–55% PERCOLL) and 4 (>55%) yielded means of 7% and 8% of the original samples, respectively. This represents 20% and 24% of the nonadherent cells. The total yield of all fractions was 58% of the nonadherent cells. CD3 positive cells (T cells) were decreased in low density fractions (mean 6% in FR.1) as compared to bone marrow separated by FICOLL (Mean 17%). In contrast, CD3-positive cells were increased in high density fractions (33% in FR.4, Table I). Similarly, CD4 and CD8-positive cells were reduced in the low density fraction (both 2% in FR.1) as compared to bone marrow separated by FICOLL (both 9%), and to high density PERCOLL fractions (both 15% in FR.4). In contrast, CD16-positive cells (NK cell marker) were enriched in low density fractions (21% in FR.2) as compared to high density fractions (4% in FR.4).

In an additional experiment, plastic-nonadherent bone marrow cells were depleted of $CD33^+$ and glycophorin $A^+$ (myeloid cells) by magnetic adherence. The depleted cells were purified further by PERCOLL density gradient fractionation, and compared to PBL prepared from the same donor. Cells were strained for $TCR\alpha\beta$ and counterstained for CD4 and CD8 markers.

Table IB shows the result of a PERCOLL fractionation using 5% steps ranging from 45–55% PERCOLL prepared as above.

TABLE IB

Percentages of $CD4^+$ or $CD8^+$ $\alpha\beta^+$ and $CD4^-$ $CD^-$ $\alpha\beta^+$ Cells in Fractionated Bone Marrow and PBL

| | Percentage of Cells Expressing Surface Marker[a] | | |
|---|---|---|---|
| Fraction | $CD4^+$ $\alpha\beta^+$ and $CD8^+$ $\alpha\beta^+$ | $CD4^-$ $CD8^-$ $\alpha\beta^+$ | Ratio[b] |
| FICOLL Gradient and "Panning" | 24 | 0.54 | 47 |
| PERCOLL Gradient | | | |
| FR.1 | 12 | 0.8 | 15 |
| FR.2 | 17 | 0.6 | 28 |
| FR.3 | 34 | 1.2 | 28 |
| FR.4 | 19 | 0.4 | 47 |
| PBL | 65 | 1.0 | 65 |

[a]Percentage of cells staining positively for given surface marker in one of two similar experiments in which T cells in bone marrow were enriched by depletion of $CD33^+$ and glycophorin $A^+$ cells using magnetic beads. The same thresholds were used in all experiments.
[b]The ratio of $CD4^+$ $\alpha\beta$ or $CD8^+$ $\alpha\beta^+$: $CD4^-$ $8^-$ $\alpha\beta^+$ cells was determined.

An average of 65% of PBL were $CD4^+$ $\alpha\beta^+$ and $CD8^+$ $\alpha\beta^+$ cells, and $CD4^-$ and $CD8^-$ $\alpha\beta^+$ represented 1.0%. The average ratio of $CD4^+$ or $CD8^+$ $\alpha\beta^+$:$CD4^-$ $CD8^-$ $\alpha\beta^+$ was approximately 65:1. In contrast the ratio of $CD4^+$ or $CD8^+$ $\alpha\beta^+$:$CD4^-$ $CD8^-$ $\alpha\beta^+$ cells in the low density bone marrow fraction 1 was 15:1, and rose to 28:1 and 47.1 in the high density fractions 3 and 4, respectively. The change in ratio is mainly due to a depletion of $CD4^+$ and $CD8^+$ cells in the low density fractions without a depletion of $CD4^-$ $CD8^-$ $\alpha\beta^+$ cells.

In an additional experiment, conducted as described above, but substituting 2.5% steps in the PERCOLL gradient and a 40–50% PERCOLL range, cells were tested for the presence of CD34 markers as well as the background concentration of $CD3^+$, $CD4^+$, $CD8^+$ marked cells. The results in Table II show enrichment for the $CD34^+$ marked cells in the lower percentage PERCOLL fractions with some variation between patients. These separations were conducted on cells prepared by a modification of the foregoing procedure wherein bone marrow cells were first treated with heta starch solution to remove red blood cells followed by a FICOLL-HYPAQUE gradient for removal of polymorphonuclear cells. Generally, substantial numbers of cells were recovered although the percentage of total cells after the first two steps ranged from about 20% to about 75% of the total bone marrow cells.

TABLE II

% of $CD34^+$ Cells

| | Patient # | | | | | | |
|---|---|---|---|---|---|---|---|
| Fraction | 1 | 2 | 3[†] | 4[†] | 5[†] | 6[†] | 7[†] |
| Bone marrow | 0.3 | 4.9 | 1.3 | 0.5 | ND | ND | 1.2 |
| Heta Starch | 0.7 | 1.9 | 0.7 | 0.1 | ND | ND | 0 |
| FICOLL HYPAQUE | 1.1 | 2.0 | 0.2 | 2.0 | 1.2 | ND | 3.6 |
| PERCOLL: | | | | | | | |
| I (40–42.5%) | 4.5 | 15.3 | 5.2 | 6.0 | 9.9 | 25.6 | 4.3 |
| II (42.5–45%) | 13.6 | 19.6 | 25.8 | 12.7 | 6.3 | 15.6 | 9.1 |
| III (45–47.5%) | 10.1 | 7.3 | 15.2 | 6.4* | 1.2 | 7.1 | 15.0 |
| IV (4.75–50%) | 3.8 | 1.2 | 0 | 4.3 | 1.0 | 1.5 | 2.0 |
| V (>50%) | 0.2 | 0.1 | 0 | 2.5 | 0.1 | 0.1 | 1.1 |

[†]The values given are corrected for background.
*Not corrected.

As shown in Table II, PERCOLL gradients succeed in separating enriched populations of $CD34^+$ cells. These cells can be stored until needed for use to aid in graftment in autologous transplants or for stem cell replacements in patients undergoing chemotherapy. While there is variability among patients as to the fraction containing the enriched population, in general, enrichment occurs in the lowest density fractions. These fractions (I+II+III) constitute 25% of the original cell population.

As set forth above, the fractions should be assayed for the CD34 marker to verify which fractions should be retained. In the case of allogeneic transplants, in addition, the T-cell component should be assessed by monitoring CD3, CD4 and CD8.

The foregoing separation method was also applied to white blood cells that had been obtained using a commercial leukophoresis apparatus to process the blood of a cancer patient. The white blood cells obtained using the standard procedure were subjected to FICOLL-HYPAQUE gradient separation to recover only mononuclear cells and then subjected to PERCOLL gradient separation using 2.5% steps between 40–50% PERCOLL, as described above. About 15 billion cells, about 1% of which contained CD34 markers, were subjected to the PERCOLL gradient separation, and the low density fractions contained about 1.2 billion cells, about 10% of which were $CD34^+$. Thus, about 60–70% of the $CD34^+$ cells in the original population were recovered.

EXAMPLE 7

Results of MLR Using Fractionated Bone Marrow Cells as Responders

To conduct the MLR, responder and stimulator cells were cultured at a concentration of $1 \times 10^5$ cells each in a final volume of 0.2 ml per well in flat-bottom microculture plates (Costar, Cambridge, Mass.). Cultures were incubated for 120 hours at 37° C. with 5% $CO_2$. Stimulator cells were irradiated with 3000 cGy from a $^{137}Cs$ source (Mark I model 125 irradiator, J. L. Shepherd and Associates, Glendale, Calif.).

DNA synthesis was assayed by the addition of 1 μCi of tritiated thymidine ($^3$H-TCR, specific activity 6.7 Ci/mM, New England Nuclear Corp., Boston, Mass.) to each well during the final 18 hours of incubation period. Radioactivity was measured in a liquid scintillation counter (Beckman Instruments, Inc., Fullerton, Calif.). Experiments were performed in triplicate, and values are expressed as means. Standard errors were less than 10% of the mean in almost all cases.

Figure 5:
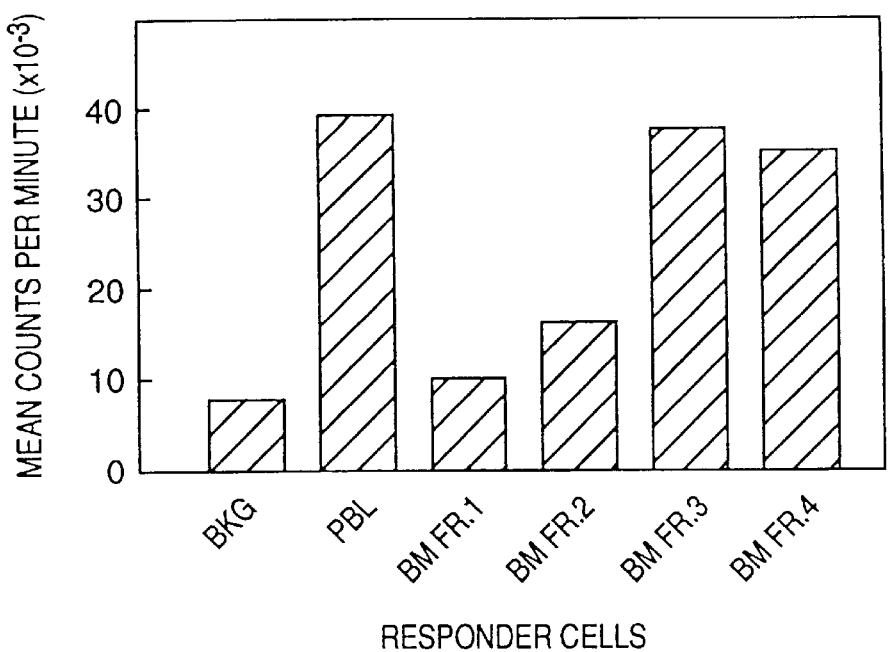
FIG. 5 shows the response of various bone marrow fractions in the MLR with allogeneic stimulator cells.

Cells from various PERCOLL fractions from Example 6 were added to irradiated allogeneic stimulator cells and tested as responder cells in the MLR. Low density PERCOLL fractions were poor responders, and $^3$H-TCR incorporation was similar to background. High density fractions gave vigorous responses which were about 3.5 times greater than that of the former. The response of high density marrow cells were similar to that of PBL (see FIG. 5).

Figure 6:
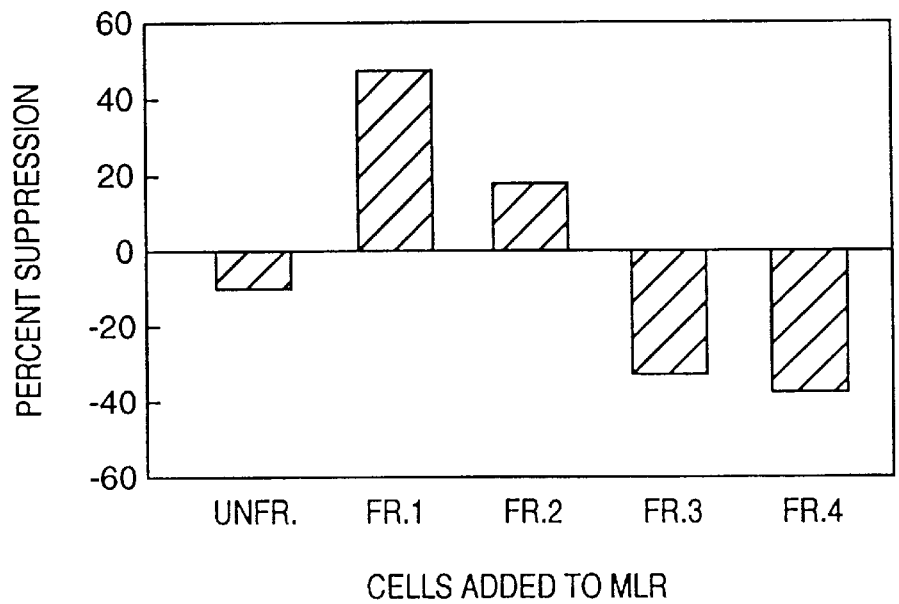
FIG. 6 shows the ability of various bone marrow fractions to suppress the MLR.

Unfractionated and low density fractions of rodent bone marrow cells have been reported to suppress the MLR (Weigenberg, M., et al., *J Immunol* (1983) 132:971–978; Noya, S. J., et al., *J Leuk Biol* (1988) 43:279–287). In the current study, the suppressive activity of unfractionated and fractionated human bone marrow cells irradiated in vitro (3000 cGy) was tested. A typical example of the effect of various PERCOLL fractions added to the MLR is shown in FIG. 6. $^3$H-TdR incorporation in the MLR without the addition of cocultured cells is set as 0% suppression. In contrast to the results in mice, unfractionated irradiated human bone marrow enhanced $^3$H-TdR incorporation by about 10% when added to the MLR. The lowest density marrow cells (FR. 1) suppressed the MLR by about 50%. High density cells of FR.3 has little effect, and high density marrow cells of FR.4 enhanced 3TdR incorporation by about 40%.

EXAMPLE 8

Ability of Cell Fractions to Suppress the MLR

In the conduct of the assay, irradiated (3000 cGy) cells to be tested were added at a variety of concentrations to 96-well, flat-bottomed microtiter plates containing 1×10$^5$ responder and 1×10$^5$ irradiated (3000 cGy) stimulator cells/well in a final volume of 200 μl. Controls included addition of irradiated responder cells instead of putative suppressor cells, or no addition of cells. Cultures were incubated at 37° C. in 5% $CO_2$. After 120 hours, plates were pulsed with 1 μCi/well $^3$H-TdR as described above. All experiments were performed in triplicate. Percentage suppression was calculated as [1-(cpm with cocultured cells)/cpm without cocultured cells]×100. Purified CD16$^+$ (bright) cells were obtained by flow cytometry from low density marrow cells (FR1 and FR2) of Example 6, and then added in graded doses to the MLR using autologous responder PBL and allogeneic stimulator PBL. In control experiments, purified CD3$^+$ (bright) cells from the low density fractions, as well as unsorted low density cells were added to the MLR. Neither the sorted CD16$^+$ nor the CD3$^+$ cells inhibited $^3$H-TdR over the dose range tested. However, the unsorted low density cells were able to suppress the response, and about 40% suppression was observed with 1×10$^5$ cocultured cells.

Since CD4$^-$ CD8$^-$ αβ$^+$ cells from the low density fractions of normal mouse bone marrow are able to suppress the MLR purified populations of sorted human CD4$^-$ CD8$^-$ αβ$^+$ cells were tested for their suppressive activity in the MLR. In order to obtain sufficient numbers of these cells, marrow cells were separated on a FICOLL gradient, and then "panned" to remove myeloid cells with anti-MO-1 (anti-CD11b) and anti-glycophorin A monoclonal antibodies. The nonadherent cells were stained with fluorescein-conjugated anti-αβ TCR and phycoerythrin- conjugated anti- CD4 and anti-CD8 antibodies. Two-color analysis of these cells was compared to similarly stained PBL from the same donor.

A discrete population of CD4$^-$ CD8$^-$ αβ$^+$ cells was observed in bone marrow cells of some donors but not with PBL. The CD4$^-$ CD8$^-$ αβ$^+$ and CD4$^-$ CD8$^-$ αβ$^{31}$ populations of marrow cells were purified by flow cytometry, and reanalyzed for their surface marker patterns. The intensity of staining for the CD4 and CD8 markers was dull in both populations and overlapped. However, the pattern for TCRαβ staining showed a clear separation of bright and dull cells such that less than 5% contamination was noted. Graded numbers of CD4$^-$, CD8$^-$, TCRαβ$^-$ and null cells were added to the MLR. Although both populations suppressed the $^3$H-TdR incorporation by about 40%, the DNS cells were approximately five times more efficient than the DNS population. Unsorted marrow cells separated on FICOLL and "panned" as above failed to suppress the MLR over the dose range tested. The lack of suppression by the unsorted cells may be related to the presence of CD4$^+$ or CD8$^+$ cells which may enhance the MLR, and to the low percentage of DNS cells.

EXAMPLE 9

Enrichment of Fractionated Bone Marrow Cells for Suppressor Activity

The fractions of bone marrow prepared as in Example 8 which are enriched in DNS are further enriched in this phenotype population by culturing in the presence of suitable growth factors. The appropriate growth factors can readily be assessed by routine supplementation of the media and testing the resulting populations for their ability to suppress the MLR.

EXAMPLE 10

Suppression of Spleen Enlargement by Cloned NS Cells

When foreign immunocompetent cells are supplied in sufficiently small amounts relative to the state of immunosuppression of the host, the foreign (donor) cells are generally not lethal to the host, but the host displays a measurable response in the form of spleen enlargement. An assay for graft-versus-host disease based on this observation was disclosed by Simonsen, M., *Prog Allergy* (1962) 6:349–467. This assay for sublethal graft-versus-host disease was used to determine the effect of TLI-2.4C and 4BA4 cell lines on this response.

To determine the proper dosage level for the donor cells, 0.5, 1, 5, or 10×10$^6$ adult C57BL/Ka spleen cells were injected into the F1 cross BALB/c×C57BL/Ka neonatal hosts. The adult (8–12 weeks old) dissociated spleen cells were prepared in tissue culture medium RPMI-1640 (Gibco, Grand Island, N.Y.) and injected intraperitoneally in 0.1 ml into the F1 cross on day 4–7 after birth. Eight days later recipient spleens were removed and assayed. Injection of 5×10$^6$ cells was shown to give an easily measurable response of the order of a 2.4-fold (average) increase in spleen size, and was on the dose responsive portion of the curve obtained, shown in FIG. 2.

Spleen indices were calculated and represent the ratio of the weight of the spleens of injected mice to the weights of uninjected litter mate controls. Indices greater than 1.0 are indication of graft-versus-host disease.

Table III shows the results obtained when the subject neonates were injected intraperitoneally with $5\times10^6$ C57BL/Ka spleen cells 4–7 days after birth with and without NS cells or control HT-2 cells and the spleen indices measured 8 days later. As expected, controls injected with $5\times10^6$ F1 hybrid spleen cells showed no spleen enlargement.

TABLE III

| Soleen Index (Mean) | |
| --- | --- |
| No addition | 2.6 |
| +15 × 10⁶ TLI-2.4C | 1.2 |
| No addition | 2.7 |
| +15 × 10⁶ 4BA4 | 1.8 |
| No addition | 2.5 |
| +15 × 10⁶ HT-2 | 2.3 |
| No addition | 2.6 |
| +5 × 10⁶ TLI-2.4C | 1.6 |
| No addition | 2.5 |
| +5 × 10⁶ HT-2 | 2.3 |

The results are clear that co-injection of either TLI-2.4C or 4BA4 cells at $15\times10^6$ cells is effective in suppressing graft-versus-host disease as measured by the spleen enlargement caused by the foreign cells. Reducing the NS cells injected to $5\times10^6$ reduced the amount of suppression but did not destroy it. A control T-cell line (HT-2) does not suppress.

EXAMPLE 11

Suppression of Lethal Graft-Versus-Host Disease by Cloned NS Cells

When similar administrations of foreign tissues are made to irradiated weanling hosts, the response is not limited to spleen enlargement, and the injections are generally fatal. Previous studies have shown that sublethally irradiated adult BALB/c mice injected IV with C57BL/Ka spleen cells are killed within two weeks. This is in part due to the high concentration of T cells in the spleen.

Figure 7:
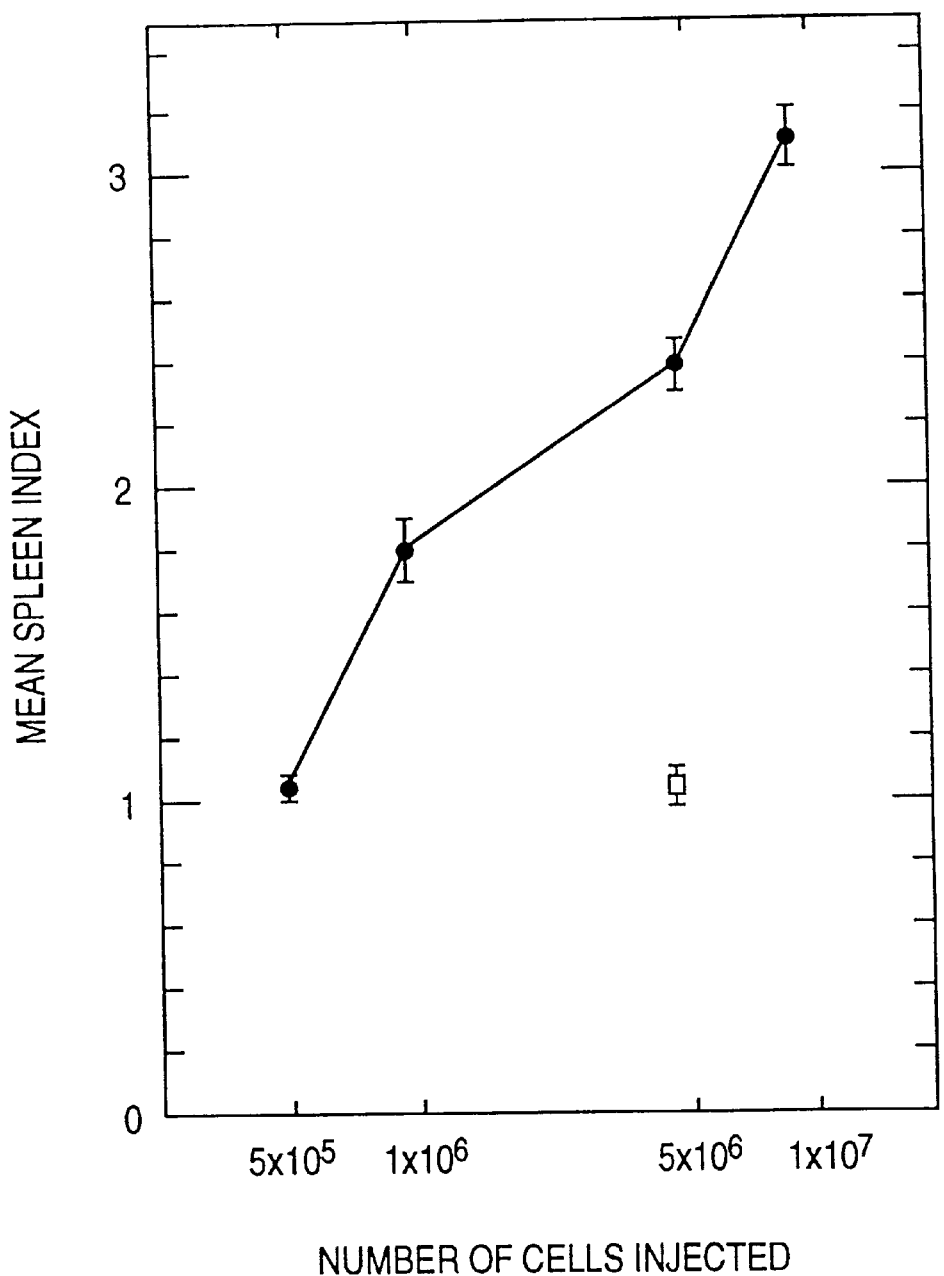
FIG. 7 shows the dose response curve for spleen enlargement as a manifestation of graft-versus-host response in neonates.
Figure 8:
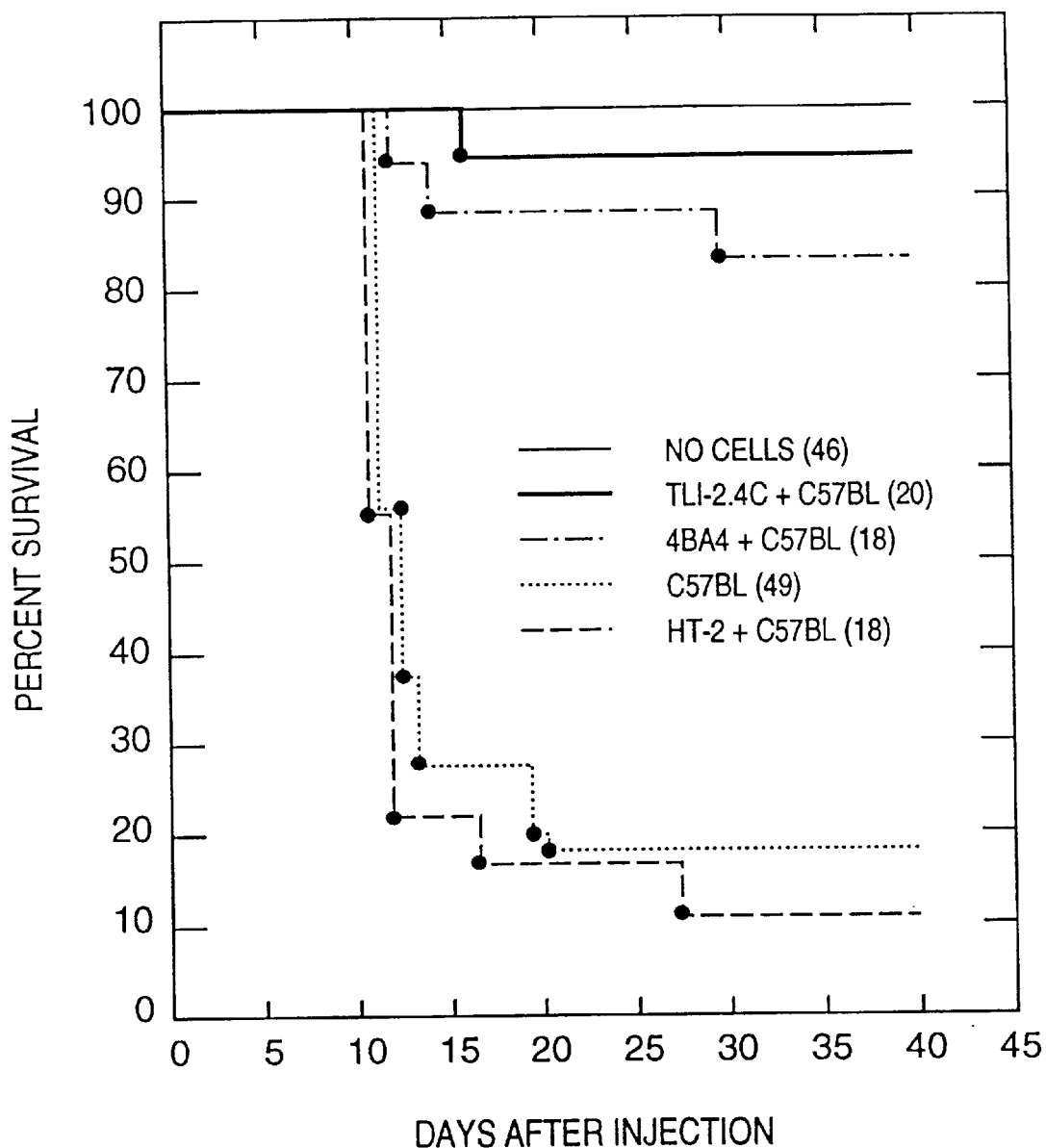
FIG. 8 shows survival rates of mice injected with allogeneic spleen cells with and without NS cells.

BALB/c weanlings were given 400 rad whole body irradiation 6–12 hours before administration of $5\times10^6$ C57BL/Ka spleen cells in 0.5 ml RPMI1640, either alone or in combination with the NS cells. Under these circumstances, BALB/c 21 day old weanlings injected intraperitoneally with C57BL/Ka spleen cells were killed (85% die by 30 days). As would be expected, C57BL/Ka weanlings similarly treated survive. However, for BALB/c mice receiving $15\times10^6$ cloned NS cells (TLI-2.4C) co-injected with the C57BL/Ka spleen cells, only 5% of the hosts died after 30 days. Co-injections of $15\times10^6$ 4BA4 cells are only slightly less effective. Co-injection with HT-2 cells gave results similar to those of the controls. These results are summarized in FIG. 7, where the numbers in parentheses show the number of mice in each group. The survival rates at 100 days were the same as those shown for 40 days in the Figure. Those few mice receiving co-injected HT-2 cells which did survive were runted.

It is clear from the foregoing results that the cloned NS cells are capable of suppressing the acute graft-versus-host disease mounted against immunocompromised hosts. (It should be noted that intraperitoneal injection of the spleen cells and of the NS cells was essential; similar experiments conducted intravenously were not successful, possibly due to failure of NS cells to migrate to the host spleen and interact with the donor cells.)

The conditions of the in vivo treatment performed above, however, did not result in the NS-cells conferring chimeric characteristics on the host. To demonstrate this, peripheral blood mononuclear (PMN) cells were assessed for the presence of C57BL/Ka donor cells. PMN were isolated from surviving hosts after 30 days of test period, and incubated with anti-C57BL/Ka antiserum with complement in a microcytotoxicity test performed as described by Slavin, S., et al., *J Exp Med* (1977) 146:34–48. Where C57BL/Ka characteristics present in any PMN cells, cell death would have resulted; however, none was observed. Also, these hosts were not capable of accepting C57BL/Ka skin grafts within 2 wk after the initial injection.

EXAMPLE 12

Cloned NS Cells Are Permissive to Establishment of Chimeric Nature and Immunotolerance While the NS cells were shown to protect subjects against the acute response produced against injection of allogeneic spleen cells, these spleen injections failed to confer the desired immunotolerance and chimerism on the host. This failure may be due to the nature of the injected tissue and thus its failure to repopulate the host bone marrow and spleen with C57BL/Ka hematopoietic stem cells. Spleen cells contain a high population of T-lymphocytes, thought to be responsible for the acute graft-versus-host disease, but a relatively low population of stem cells, which are relatively undifferentiated and are thought to be responsible for, or at least essential to, production of immunotolerance.

Accordingly, procedures similar to those above were conducted using bone marrow rather than spleen cells as the source of foreign tissue. Adult BALB/c mice were given lethal whole body irradiation (700 rad) one day before intraperitoneal injection of $50\times10^6$ C57BL/Ka bone marrow cells; with or without $15\times10^6$ TLI-2.4C cells. 12 of 14 mice survived 30 days later without evidence of graft-versus-host disease when the NS cells were co-injected. Among controls given no NS cells, 8 of 10 survived.

PMN from all surviving animals were tested by the microcytotoxicity assay as above and found to be chimeras as shown by 95% killing of PMN cells. Further, they were able to accept C57BL/Ka, but not C3H, skin grafts after 40 days.

The spleen cells of the chimeras were further tested for their ability to induce graft-versus-host disease in fresh BALB/c mice recipients. Normal C57BL/Ka donor cells, when injected at $10\times10^6$ spleen cells intraperitoneally in 0.5 ml RPMI-1640 medium into either BALB/c or C3H recipients result in the death of all mice injected within 14 days. As would be expected, control mice having no cells injected survived. Spleen cells of the chimeras, injected similarly into BALB/c or C3H mice, induced graft-versus-host disease only in the C3H recipients; the BALB/c recipients survived injection of the chimeric spleens whether derived from chimeric donors given a C57BL/Ka bone marrow injection alone or in combination with NS cells. The immunotolerance conferred on the chimeric donors was specific to BALB/c recipients.

EXAMPLE 13

Properties of Fractions of Spleen and Bone Marrow Cells

Spleen cells were removed aseptically from C57BL/Ka (H-2⁶) mice, and single cell suspensions were prepared by gently pressing the spleen fragments through a nylon fiber mesh into cold RPMI-1640 medium. Bone marrow cells were prepared by flushing the femora and tibiae of C57BL/Ka(H-2⁶) mice (4–10 weeks old) with cold RPMI-1640 medium using a 25-gauge needle. Bone marrow plugs were then gently resuspended. The cells were washed twice and counted in 2% acetic acid before use, and viability was determined by trypan blue dye exclusion.

PERCOLL (Pharmacia, Uppsala, Sweden), composed of colloidal silica coated with polyvinyl pyrrolidone, was first made isotonic for use with living lymphocytes. Calcium and magnesium-free 10×DPBS was added to the stock solution of PERCOLL in a ratio of one part (v/v) DPBS to nine parts (v/v) PERCOLL (starting density 1.130 g/ml), and it was adjusted to pH 7.2. For subsequent use, this working stock solution was progressively diluted in RPMI-1640 medium to obtain solutions containing 40, 50, 55, 60 and 70 percent of PERCOLL. Corresponding densities (g/ml) were 1.050, 1.060, 1.068, 1.075, 1.090, respectively. Two to three ml volumes of each of the PERCOLL solutions, starting with the 70% concentration and continuing with the decreasing concentrations, were layered in 15 ml clear polystyrene tubes using a 5 ml pipette. A variable number of spleen or bone marrow cells (not exceeding 100×10⁶ cells) were suspended in 300 μl of RPMI-1640 medium to layer over the PERCOLL gradients. The gradient was centrifuged at 2000 rpm (520 g) for 30 minutes at room temperature and the cells at each density interface were aspirated with a Pasteur pipette and washed with RPMI-1640. The results of gradient fractionation are shown in Table IV.

EXAMPLE 14

Use of Enriched or Sorted Fresh NS Cells to Inhibit GVHD and Promote Chimerism In the GVHD assay, three to four week old BALB/c mice received a single dose of sublethal total body irradiation (TBI) (400 rad), 6 to 18 hours prior to the i.v. infusion of cells. To induce GVHD, a single inoculum of C57BL/Ka cells was given. For suppression of GVHD, BALB/c mice were given a combination of $2.5 \times 10^6$ CF57BL/Ka spleen cells, and various doses of fractionated adult C57BL/Ka bone marrow and spleen cells obtained from discontinuous PERCOLL gradients. Control groups received only 400 rads sublethal irradiation alone, or 400 rads sublethal irradiation and $2.5 \times 10^6$ syngeneic (BALB/c) unfractionated spleen cells. Mortality in all groups was recorded daily.

One hundred days after cell transfer in the GVHD assays, surviving mice were assayed for the presence of donor-type lymphocytes in the peripheral blood, identified by a complement-dependent microcytotoxicity assay. Recipients were bled from the retro-orbital sinus, and blood samples were heparinized. FICOLL-HYPAQUE gradient purified peripheral blood lymphocytes were incubated for 30 minutes at 37° C. with BALB/c anti-C57BL antiserum (final dilution 1:10) prepared as described by Okada, S., et al., *Transplantation* (1983) 36:417. After the incubation, Low-Tox-M rabbit complement (Accurate Chemicals and Scientific Co., Hicksville, N.Y.) diluted 1:4 was added to the samples. The

TABLE IV

PERCOLL Fractionation of Spleen and Bone Marrow Cells:
Percent Yield and Percent of Thy-1⁺ Cells in Each Fraction

| Percent PERCOLL (v/v) | Density of Percoll (g/ml) | Percent Yield of Spleen Fraction (Range)ᵃ | % Thy-1.2 Positive Cells In Spleen Fraction (Range)ᵇ | Percent Yield of Bone Marrow (Range)ᵃ | % Thy-1.2 Positive Cells In Bone Marrow (Range)ᵇ |
|---|---|---|---|---|---|
| 40 | 1.050 | 1–2 | 17–25 | 1–2 | 12–15 |
| 50 | 1.060 | 2–4 | 17–25 | 1–3 | 15–16 |
| 55 | 1.068 | 5–8 | 25–30 | 29–45 | 13–17 |
| 60 | 1.075 | 17–29 | 46–60 | 15–23 | 7–12 |
| 70 | 1.090 | 5–7 | 60–75 | 1–4 | ND |

ᵃPercent yield determined by number of cells applied to gradient as compared to the number obtained from each fraction. Range was determined from two to six independent experiments.
ᵇRange is shown for three independent experiments.

The fractions were also stained for the presence of CD4, CD8 and TCRαβ surface markers using monoclonal antibodies. Cells that are αβ TCR in the unfractionated spleen stain brightly for all three surface markers (41% of total cells). Unfractionated bone marrow cells contained less than 1% of cells with a similar bright staining pattern for all three T-cell surface markers. The majority of bone marrow T cells which stained positively for the αβ TCR were CD4⁻ and CD8⁻.

Analysis of bone marrow fractions showed little change in the staining pattern of T cells, since the αβ TCR⁺ CD4⁻ CD8⁻ cells were predominant in both high and low density factions. Spleen cell fractions contained brightly staining CD4⁺, CD8⁺ and αβ TCR⁺ cells as most abundant (38%) in the high density fraction (FR60) and depleted (12%) in the low density fraction (FR50). A substantial percentage (13%) of αβ TCR⁺ CD4⁻ CD8⁻ cells was in the low density fraction (FR50). The predominant T-cell subset in the bone marrow can also be found in the spleen, but the predominant spleen subset was undetectable in the marrow.

reaction mixture was again incubated at 37° C. for 45 minutes. Cells were harvested in medium containing trypan blue, and the viability of cells observed in a standard hemocytometer. The net cytotoxicity was calculated by comparing the number of viable cells present after treatment with antiserum with the number present after treatment with normal BALB/c serum. Control cytotoxicity tests with normal C57BL/Ka mice gave values of >95%, and with normal BALB/c mice gave values of <5%.

After induction of GVHD by unfractionated C57BL spleen cells in sublethally (400 rads) irradiated BALB/c hosts, none of the recipients given $2.5 \times 10^6$ cells survived more than 11 days. Approximately 50% given $1 \times 10^6$ cells survived more than 100 days, and 100% given $0.5 \times 10^6$ cells more than 100 days. Recipients given $2.5 \times 10^6$ or $5 \times 10^6$ unfractionated C57BL bone marrow cells, or no cells all survived more than 100 days.

The in vivo GVHD inductive capacity of the different spleen cell factions were measured by injecting (intravenously) $2.5 \times 10^6$ cells into sublethally irradiated BALB/c recipients. All animals given $2.5\times10^6$ spleen cells from FR40 or FR50 survived more than 100 days, and none showed obvious clinical signs of GVHD, such as ruffled fur, hunched back, facial swelling, diarrhea, hair loss or cachexia. All the BALB/c recipients injected with $2.5\times10^6$ spleen FR55 cells died by day 20, and none of the animals which received $2.5\times10^6$ FR60 cells survived more than 10 days. All the control animals injected with $2.5\times10^6$ unfractionated C57BL/Ka spleen cells died by 11 days, and the recipients given 400 rads sublethal irradiation alone survived 100 days.

None of the high or low density fractions induced lethal GVHD during the 100-day observation period.

C57BL/Ka bone marrow fractions were tested for their capacity to suppress GVHD induced by $2.5\times10^6$ unfractionated C57BL/Ka spleen cells. Coinjection of $2.5\times10^6$ FR60 or FR50+55 bone marrow cells into sublethally irradiated BALB/c recipients allowed more than 60 percent of the animals to survive more than 100 days. The greatest protection was observed with the lower density fraction (more than 80% survival). A variable proportion of the recipients that survived more than 100 days showed signs of mild chronic GVHD, including ruffled fur, hair loss, and weight loss depending on the individual experiment. Approximately 20 percent of the recipients coinjected with $2.5\times10^6$ unfractionated bone marrow cells survived more than 100 days. All BALB/c recipients which received $2.5\times10^6$ C57BL/Ka unfractionated spleen cells alone died by day 21, but all animals given irradiation alone or irradiation plus $2.5\times10^6$ syngeneic (BALB/c) unfractionated spleen cells survived more than 100 days.

The C57BL/Ka spleen cells fractionated on PERCOLL gradients ($2.5\times10^6$ cells from each fraction) were coinjected with $2.5\times10^6$ unfractionated C57BL spleen cells into sublethally irradiated BALB/c recipients. Both FR40 and FR50 allowed more than 80% of recipients to survive for more than 100 days. On the other hand, none of the recipients survived more than 20 days when $2.5\times10^6$ FR55 or FR60 cells were coinjected with the unfractionated spleen cells. All control animals that received $2.5\times10^6$ unfractionated spleen cells alone died by day 20, but all recipients given radiation alone or radiation and $2.5\times10^6$ BALB/c unfractionated spleen cells survived more than 100 days.

Graded numbers of FR50 spleen cells were coinjected with a constant number ($2.5\times10^6$) of unfractionated C57BL spleen cells into sublethally irradiated BALB/c recipients. Coinjection of $2.5\times10^6$ FR50 cells allowed more than 80 percent of the BALB/c recipients to survive for more than 100 days. Coinjection of $1\times10^6$ and $0.5\times10^6$ cells resulted in 70 and 50 percent survival for 100 days, respectively. However, 90 percent of the animals coinjected with $0.1\times10^6$ cells died of GVHD within 20 days. All the animals which received $2.5\times10^6$ unfractionated spleen cells alone died within 21 days, but all the control animals given sublethal irradiation alone survived more than 100 days.

Several groups of BALB/c recipients were tested for chimerism at 100 days using BALB/c anti-C57BL/Ka polyclonal antibody and complement. Recipients of unfractionated C57BL/Ka bone marrow alone or C57BL/Ka bone marrow fractions (Group 1) alone, or spleen fractions (Group 5) alone were not chimeric, but the groups which received unfractionated C57BL/Ka spleen cells plus low density bone marrow (Group 2; FR50) or spleen (Group 3; FR40, Group 4; FR50) cells were chimeric with a mean of 73, 74 and 91 percent donor-type cells, respectively. In addition, fresh FACS sorted cells shown to have the CD4$^-$, CD8$^-$ $\alpha\beta^+$ phenotype are demonstrated to inhibit GVHD, and promote chimerism.

Skin grafts applied to recipients shown to be chimeric with respect to the donor skin were able to tolerate the grafts indefinitely; however, nonchimeric recipients rejected such grafts, and grafts derived from donor types not related to the chimera were rejected within three weeks.

EXAMPLE 15

Characteristics of Murine Bone Marrow T Cells with Suppressor Activity

A publication by Palathumpat, V., et al., *J Immunol* (1992 148:373–380, the contents of which are incorporated herein by reference, characterizes the suppressor cells in murine bone marrow. The study showed that the predominant T cell subset in the bone marrow of specific pathogen-free C57BL/Ka and BALB/c mice had the DNS surface phenotype. These DNS cells, when obtained by cell sorting, were successful in suppressing the mixed lymphocyte reaction. The percentage of typical T cells in the spleen was reduced in adult nude mice or normal neonatal mice, as compared to the normal adult; however, the percentage of cells with the DNS phenotype in the spleen and marrow was not.

The predominant subset of marrow T cells in pathogen-free mice differ with regard to surface marker phenotype, function, dependence on adult thymus, and deletion of certain self-reactive V$\beta$ receptors when compared to typical cell T cells. The marrow T cells appeared to develop directly form marrow precursors without rearranged $\beta$ chains during a 48 hour in vitro culture.

EXAMPLE 16

Effect of Subsets of T Cells in Adult Mouse Bone Marrow and Spleen with Respect to GVHD In an additional publication by Palathumpat, V., et al., in *J Immunol* (1992) 148:373–380, the disclosure of which is incorporated herein by reference, fractionation of normal adult mouse spleen and bone marrow cells from C57BL/Ka mice was performed by discontinuous PERCOLL density gradients. Spleen cells in the fraction of 1.150–1.060 g/ml completely suppressed acute lethal GVHD when coinjected with unfractionated C57BL/Ka spleen cells into sublethally irradiated (400 rad) BALB/c mice. As few as $5\times10^7$ of these low density cells suppress acute GVHD induced by $2.5\times10^6$ unfractionated allogeneic spleen cells.

On the other hand, the high density fraction of spleen cells, 1.075–1.090 g/ml induced acute GVHD in sublethally irradiated BALB/c recipients.

Fractionation of C57BL/Ka bone marrow cells showed that none of the high or low density fractions or the unfractionated cells induced lethal GVHD. Furthermore, fractions of all recovered densities protected BALB/c recipient mice from GVHD when coinjected with C57BL/Ka unfractionated spleen cells; unfractionated bone marrow cells were modestly protective. The low density bone marrow fraction (1.050–1.068 g/ml) showed reproducible protection could be achieved at a 5:1 ratio of inducing to suppressing cells.

The low density fractions of both bone marrow and spleen cells had marked depletion of TCR$\alpha\beta$, CD4$^+$ or CD8$^+$ T cells in a predominant population of cells with a DNS phenotype. Purified populations of these DNA cells suppressed GVHD. Furthermore, recipients given unfractionated C57BL/Ka spleen cells and protected with low density bone marrow or spleen cells were chimeras, and can accept allogeneic transplants.

EXAMPLE 17

Purification of SF

The TLI-2.C7 clone was derived from the spleen of an adult BALB/c mouse given total lymphoid irradiation (TLI).

Cells were expanded in IL-2 enriched medium without addition of exogenous antigen, cloned by limiting dilution, and expressed CD4$^-$ CD8$^-$ αβ$^+$ cell surface marker phenotype. The cell line was maintained in RPMI-1640 supplemented with heat inactivated 10% FCS, 10 mM HEPES, 2 mM glutamine and 5×10$^{-5}$ M 2-ME. For culture supernatants from concanavalin A stimulated rat spleen cells (CAS) (30% v/v) were added to the medium.

The TLI-2.C7 cells were grown to confluence in medium enriched with CAS in T-75 flasks. PMA (10 ng/ml) and A23187 (0.26 μg/ml) were dissolved in RPMI 1640 supplemented with 10% heat inactivated FCS and added to the cells in a final volume of 20 ml/flask. After incubation for four hours, the cells were washed five times with PBS and overlaid with RPMI-1640 containing no additional proteins. The crude supernatants were collected 24 hours later and kept frozen at −40° C. until use.

Two liter pools of supernatants were incubated with 7 mg/ml silicic acid in PBS for 4 hours at 4° C. with continuous stirring. The silicic acid was then spun down and the nonadsorbed material was collected and concentrated in Centricel Filtration units (Polysciences, Inc., Warrington, Pa.) with a m.w. cutoff of 10 kDa; 0.1 mM PMSF was added to prevent degradation.

Figure 9:
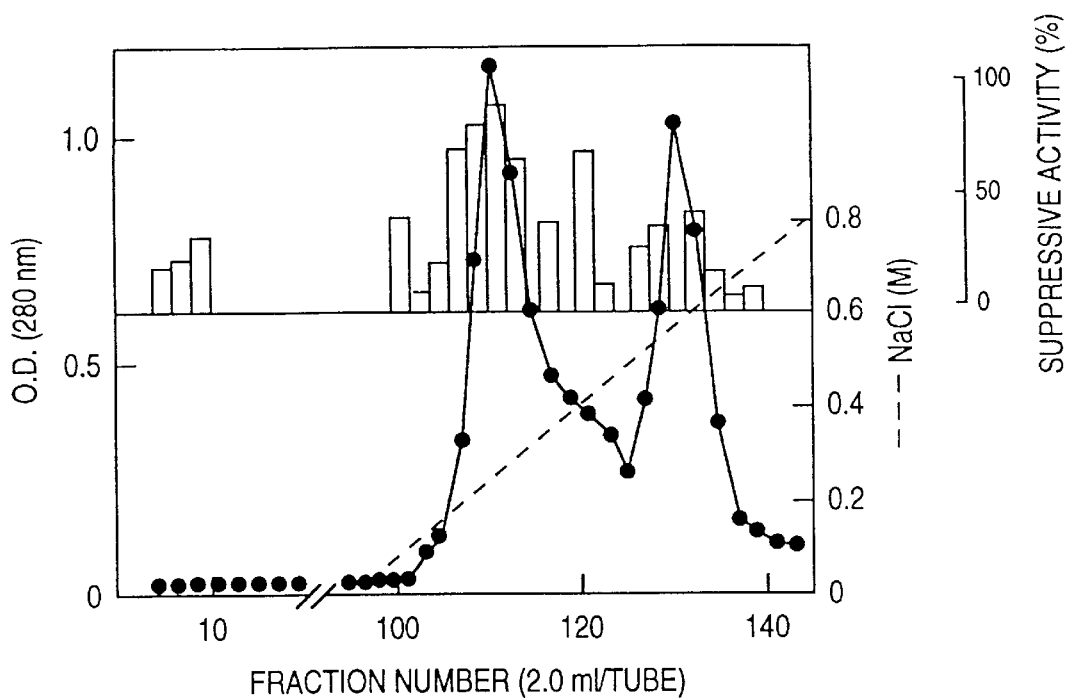
FIG. 9 shows the elution pattern for the soluble factor of the invention from DEAE Sepharose.

The nonadsorbed supernatant was dialyzed against 20 mM Tris-HCl (pH 8.0) buffer supplemented with 1 mM PMSF, and run on a DEAE-Sepharose column at 4° C. using the same buffer. After a wash with 2 bed volumes of starting buffer, the adsorbed material was eluted at a flow rate of 0.35 ml/min with a linear gradient (0–1.0 M) of NaCl, 20 mM Tris-HCl buffer (pH 8.0). Fractions of 2 ml were collected and stored at 4° C. until use in the bioassay, or frozen at −70° C. for later study. The different fractions were added to the MLR at a final 1/5 dilution and the MLR supernatants screened for IL-2 after 72 hours in the HT-2 assay using ($^3$H)-TdR incorporation. The elution portion is shown in FIG. 9; fractions eluting at 0.2–0.4 NaCl showed activity; two protein peaks eluted, one corresponding to the activity.

Figure 10:
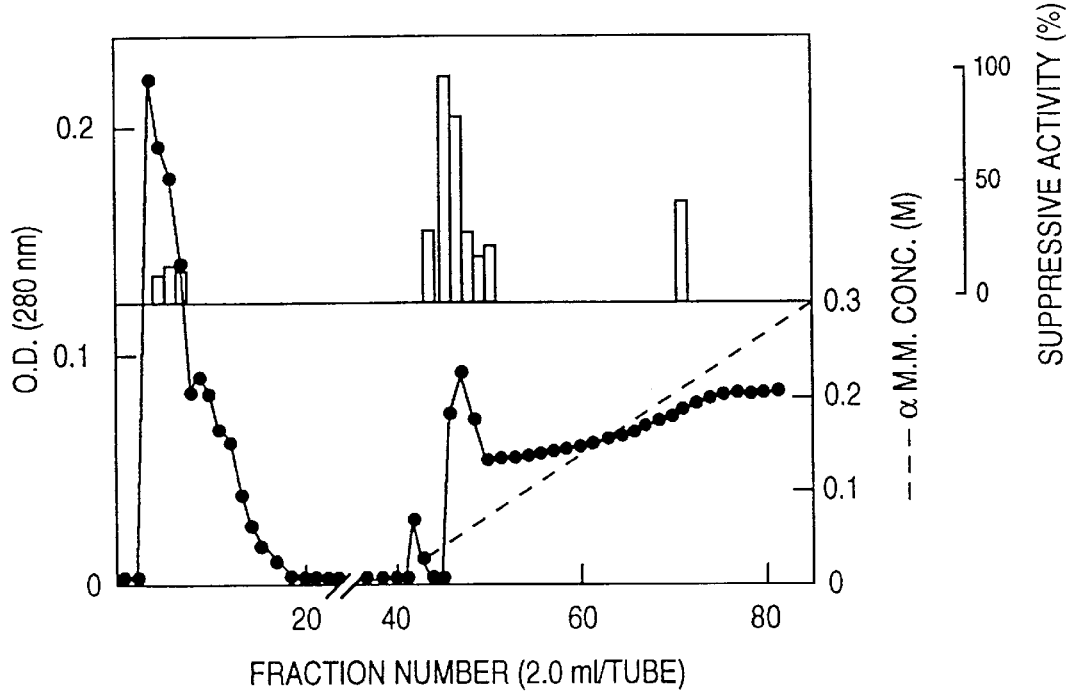
FIG. 10 shows the elution pattern for the soluble factor of the invention from lentil lectin.

The fractions containing activity were pooled, dialyzed against 5 mM Tris-HCl, 1 mM PMSF, pH 8.0 buffer, and applied to a lentil-lectin SEPHAROSE (agarose beads) 4B column equilibrated in the same buffer. After washing with 4 bed volumes of starting buffer, bound proteins were eluted with a linear gradient (0–0.3 M) of α-methyl-D-mannoside in the same buffer at a flow rate of 0.20 ml/min. Fractions of 2 ml were collected and assayed as described above. The elution pattern is drawn in FIG. 10. Only two fractions contained appreciable activity, as shown. Table V summarizes the purification steps.

suppressive activity; additional gels were run in parallel under reducing and nonreducing conditions with 50 ng of protein to identify bands by silver stain. Two bands were visualized at approximately 20 kd (dense band) and 40 kd (light band) in three separate experiments. Assays of the suppressive activity showed activity associated with the 20 kd region, some activity was in a higher molecular weight region not associated with a distinct silver-stain band.

Approximately 4 μg of the lentil-lectin pooled sample was subjected to N-terminal Edman degradation using an automated peptide sequencer. A major and a minor amino acid sequence was observed consistent with SDS-PAGE which showed a major 20 kd band, and a minor 40 Kd band. The major amino acid sequence (SEQ. ID NO:1) was X-Glu-Asn-Val-Gly-Leu-Asn-Glu-Val-Val-(Ala/Phe)-Leu-(Lys/Leu)-Tyr-Gln-Val. The amino acid in the first position could not be clearly distinguished.

EXAMPLE 18

Preparation of Antibodies

Antibodies were prepared by immunization with the peptides (SEQ. ID NO:2) Leu-Asn-Glu-Val-Val-Ala-Leu-(Lys/Leu)-Tyr-Gln-Val which were conjugated to core polymer matrix (Ala-Lys$_7$-Gly$_3$).

Male New Zealand rabbits were immunized with subcutaneous injections of one of the two synthetic peptides; first with 100 μg of the synthetic peptide conjugates mixed with an equal volume of Freund's complete adjuvant. Ten days later, the animals were bled, and the injection was repeated with the antigen mixed in an equal volume of Freund's incomplete adjuvant. Ten days later, the animals were bled, and after a third cycle, the rabbits were sacrificed and blood was allowed to clot and spun at 3,000 rpm for 20 min. The serum was loaded on an AFFI-GEL (agarose) Protein A column (Bio-Rad Inc.), previously equilibrated with PBS. The column was washed with 5 volumes of PBS, and the IgG antibodies were eluted with an acid wash consisting of 0.3 M glycine-HCl pH 2.8.

IgG serum antibodies used below were obtained 10 days after the first immunization. A single band was detected by Western blot using post-bleed but not with pre-bleed antibodies corresponding to the 20 kd band in both the DEAE and lentil-lectin eluates separated by SDS-PAGE. Rabbit serum IgG antibodies obtained after, but not before, immunization with peptide bound on Western blot to lentil lectin purified material described above which was further purified with HPLC to obtain a 20 kd fraction.

Pre-bleed and post-immunization IgG serum antibodies were conjugated to AFFI-GEL 10 and incubated overnight

TABLE V

Purification of NSF

| Purification Step | Volumes (ml) | Total Protein (mg) | Total Suppress-ive (U) | Specific Activity (U/mg) | Purification (fold) | Recovery (%) |
|---|---|---|---|---|---|---|
| Supernatant | 2,000 | 56.6 | 80,000 | 1,410 | 1 | 100 |
| Silicic Acid | 1,980 | 21.0 | 150,000 | 7,540 | 5 | 198 |
| DEAE-Sepharose | 16 | 0.160 | 10,240 | 64,000 | 45 | 13 |
| Lentil-Lectin | 6 | 0.019 | 7,440 | 387,500 | 275 | 91a |

Overall, a 275-fold purification and 9% yield were achieved.

Aliquots of the pooled active fractions containing 500 ng protein eluted from the lentil-lectin column were separated by SDS-polyacrylamide (12.5%) gel electrophoresis under non-reducing conditions. The gels were sliced, aliquots were eluted from each fragment, and the eluates were assayed for with crude TLI-2C7 supernatants that showed high levels of suppressive activity. While untreated crude supernatant completely inhibited IL-2 secretion in the MLR up to a dilution of 1:2048, and showed 50% inhibition at a dilution of 1:8192, after incubation with coupled antibodies, no suppressive activity was observed even at 1:32 dilution.

I claim:

1. A human cell line including the progeny thereof comprising, double negative suppressor cells which inhibit the mixed lymphocyte reaction in vitro, but do not kill corresponding target cells, wherein said double negative suppressor cells are characterized by a surface marker pattern which is IL-2R$^+$, Ig$^-$, CD4$^-$, CD8$^-$, CD3$^+$, MAC-1$^-$, TCRαβ$^+$.

2. A cellular composition for suppressing an immune response comprising human suppressor cells which are depleted of radiosensitive suppressor cells and null suppressor cells characterized by a phenotype of CD4$^-$, CD8$^-$, CD3$^-$ and TCRαβ$^-$, with the retention of double negative suppressor cells which inhibit the mixed lymphocyte reaction in vitro, but do not kill corresponding target cells, wherein said double negative suppressor cells are characterized by a surface marker pattern of IL-2R$^+$, CD3$^+$, TCRαβ$^+$, Ig$^-$, CD4$^-$, CD8$^-$ and MAC-1$^-$.

3. The cellular composition of claim 2, which further comprises CD34$^+$ progenitor cells.

4. A human cell population consisting essentially of human suppressor cells of the double negative phenotype characterized by a surface marker pattern of IL-2R$^+$, Ig$^-$, CD4$^-$, CD8$^-$, CD3$^+$, MAC-1$^-$ and TCRαβ$^+$.

5. A method to prepare a cellular composition which suppresses the mixed lymphocyte reaction in vitro, which method comprises:

(a) subjecting a cell suspension prepared from a human blood cell source to treatment to deplete said cell suspension of any red blood cells;

(b) subjecting the cell suspension resulting from step (a) to separation to deplete any polymorphonuclear cells and recover mononuclear cells; and (c) subjecting the mononuclear cells recovered in step (b) to separation to deplete radiosensitive suppressor cells and null suppressor cells characterized by a phenotype of $CD4^-$, $CD8^-$, $CD3^-$ and $TCR\alpha\beta^-$ and recover double negative suppressor cells characterized by a surface marker pattern of $CD4^-$, $CD8^-$, $CD3^+$ and $TCR\alpha\beta^+$.

6. The method of claim 5 wherein said blood cell source is bone marrow or blood.

7. A population of cells which suppresses the mixed lymphocyte reaction prepared by the method of claim 6.

8. A method to prepare a cell population consisting essentially of human double negative suppressor cells, which method comprises:

(a) subjecting a cell suspension prepared from a human blood cell source to a 47.5% colloidal silica density gradient and recovering the cells which are contained in a density fraction lower than 47.5% of said gradient that is enriched for suppressor cells as compared to other T cells;

(b) staining the cells recovered in step (a) for CD4, CD8 and $TCR\alpha\beta$;

(c) subjecting said stained cells to flow cytometry to identify double negative suppressor cells; and (d) recovering the double negative suppressor cells.

9. A population consisting essentially of double negative suppressor cells prepared by the method of claim 8.

10. A method to prepare a cell population consisting essentially of human double negative suppressor cells, which method comprises:

(a) subjecting a cell suspension prepared from a human blood cell source to sucrose polymer density gradient separation;

(b) recovering the mononuclear cell fraction of said gradient;

(c) depleting mononuclear cell fraction of myeloid and erythroid cells;

(d) staining the remaining cells of the fraction resulting from step (c) for CD4, CD8 and $TCR\alpha\beta$;

(e) subjecting said stained cells to flow cytometry to identify double negative suppressor cells; and (f) recovering the double negative suppressor cells.

11. A population consisting essentially of double negative suppressor cells prepared by the method of claim 10.

12. A method to expand cell number of a population of human double negative suppressor (DNS) cells, comprising treating a population of human DNS cells depleted of radiosensitive suppressor cells and null suppressor cells characterized by a phenotype of $CD4^-$, $CD8^-$, $CD3^-$ and $TCR\alpha\beta^-$ with at least one cytokine, said DNS cells are characterized by a surface marker pattern of $IL-2R^+$, $Ig^-$, $CD4^-$, $CD8^-$, $CD3^+$, $MAC-1^-$ and $TCR\alpha\beta^+$.

* * * * *